(12) United States Patent
Dykes

(10) Patent No.: US 9,902,949 B2
(45) Date of Patent: *Feb. 27, 2018

(54) METHODS FOR UNIVERSAL TARGET CAPTURE

(71) Applicant: DNAE Group Holdings Limited, London (GB)

(72) Inventor: Colin Dykes, Albuquerque, NM (US)

(73) Assignee: DNAE Group Holdings Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/254,537

(22) Filed: Sep. 1, 2016

(65) Prior Publication Data
US 2016/0369265 A1    Dec. 22, 2016

Related U.S. Application Data

(63) Continuation of application No. 14/107,335, filed on Dec. 16, 2013, now Pat. No. 9,434,940.

(60) Provisional application No. 61/739,567, filed on Dec. 19, 2012.

(51) Int. Cl.
| | | |
|---|---|---|
| *C12Q 1/04* | (2006.01) | |
| *C12N 15/10* | (2006.01) | |
| *G01N 33/68* | (2006.01) | |
| *G01N 33/543* | (2006.01) | |

(52) U.S. Cl.
CPC ........... *C12N 15/1037* (2013.01); *C12Q 1/04* (2013.01); *G01N 33/54333* (2013.01); *G01N 33/6845* (2013.01); *G01N 2333/005* (2013.01)

(58) Field of Classification Search
None
See application file for complete search history.

(56) References Cited

U.S. PATENT DOCUMENTS

| | | |
|---|---|---|
| 3,970,518 A | 7/1976 | Giaever |
| 4,018,886 A | 4/1977 | Giaever |
| 4,180,563 A | 12/1979 | Fauve |
| 4,230,685 A | 10/1980 | Senyei et al. |
| 4,267,234 A | 5/1981 | Rembaum |
| 4,434,237 A | 2/1984 | Dinarello |
| 4,452,773 A | 6/1984 | Molday |
| 4,551,435 A | 11/1985 | Liberti et al. |
| 4,554,088 A | 11/1985 | Whitehead et al. |
| 4,659,678 A | 4/1987 | Forrest et al. |
| 4,677,055 A | 6/1987 | Dodin et al. |
| 4,683,195 A | 7/1987 | Mullis et al. |
| 4,683,202 A | 7/1987 | Mullis |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Harada, et al., Monoclonal antibody G6K12 specific for membrane-associated differentiation marker of human stratified squamous epithelia and squamous cell carcinoma, J. Oral. Pathol. Med., 22(4):1145-152 (1993).

(Continued)

*Primary Examiner* — Nianxiang Zou
(74) *Attorney, Agent, or Firm* — Brown Rudnick LLP; Thomas C. Meyers

(57) ABSTRACT

The invention generally relates to methods for universal target capture.

14 Claims, 7 Drawing Sheets

(56) References Cited

U.S. PATENT DOCUMENTS

| | | |
|---|---|---|
| 4,695,393 A | 9/1987 | Chagnon et al. |
| 4,795,698 A | 1/1989 | Owen et al. |
| 4,851,330 A | 7/1989 | Kohne |
| 4,901,018 A | 2/1990 | Lew |
| 4,925,788 A | 5/1990 | Liberti |
| 4,942,124 A | 7/1990 | Church |
| 4,988,617 A | 1/1991 | Landegren et al. |
| 5,004,699 A | 4/1991 | Winters |
| 5,047,321 A | 9/1991 | Loken et al. |
| 5,057,413 A | 10/1991 | Terstappen et al. |
| 5,089,386 A | 2/1992 | Stackebrandt et al. |
| 5,108,933 A | 4/1992 | Liberti et al. |
| 5,136,095 A | 8/1992 | Tarnowski et al. |
| 5,149,625 A | 9/1992 | Church et al. |
| 5,164,297 A | 11/1992 | Josephson et al. |
| 5,186,827 A | 2/1993 | Liberti et al. |
| 5,200,084 A | 4/1993 | Liberti et al. |
| 5,229,724 A | 7/1993 | Zeiger |
| 5,234,816 A | 8/1993 | Terstappen |
| 5,242,794 A | 9/1993 | Whiteley et al. |
| 5,254,460 A | 10/1993 | Josephson et al. |
| 5,270,163 A | 12/1993 | Gold et al. |
| 5,338,687 A | 8/1994 | Lee et al. |
| 5,342,790 A | 8/1994 | Levine et al. |
| 5,460,979 A | 10/1995 | Levine et al. |
| 5,466,574 A | 11/1995 | Liberti et al. |
| 5,494,810 A | 2/1996 | Barany et al. |
| 5,512,332 A | 4/1996 | Liberti et al. |
| 5,541,072 A | 7/1996 | Wang et al. |
| 5,583,024 A | 12/1996 | McElroy et al. |
| 5,583,033 A | 12/1996 | Terstappen et al. |
| 5,597,531 A | 1/1997 | Liberti et al. |
| 5,604,097 A | 2/1997 | Brenner |
| 5,605,805 A | 2/1997 | Verwer et al. |
| 5,622,831 A | 4/1997 | Liberti et al. |
| 5,622,853 A | 4/1997 | Terstappen et al. |
| 5,636,400 A | 6/1997 | Young |
| 5,646,001 A | 7/1997 | Terstappen et al. |
| 5,654,636 A | 8/1997 | Sweedler et al. |
| 5,660,990 A | 8/1997 | Rao et al. |
| 5,674,713 A | 10/1997 | McElroy et al. |
| 5,677,133 A | 10/1997 | Oberhardt |
| 5,681,478 A | 10/1997 | Lea et al. |
| 5,684,401 A | 11/1997 | Peck et al. |
| 5,695,934 A | 12/1997 | Brenner |
| 5,695,946 A | 12/1997 | Benjamin et al. |
| 5,698,271 A | 12/1997 | Liberti et al. |
| 5,700,673 A | 12/1997 | McElroy et al. |
| 5,741,714 A | 4/1998 | Liberti |
| 5,768,089 A | 6/1998 | Finnigan |
| 5,770,461 A | 6/1998 | Sakazume et al. |
| 5,773,307 A | 6/1998 | Colin et al. |
| 5,776,710 A | 7/1998 | Levine et al. |
| 5,795,470 A | 8/1998 | Wang et al. |
| 5,821,066 A | 10/1998 | Pyle et al. |
| 5,834,217 A | 11/1998 | Levine et al. |
| 5,840,580 A | 11/1998 | Terstappen et al. |
| 5,846,719 A | 12/1998 | Brenner et al. |
| 5,863,722 A | 1/1999 | Brenner |
| 5,866,099 A | 2/1999 | Owen et al. |
| 5,869,252 A | 2/1999 | Bouma et al. |
| 5,876,593 A | 3/1999 | Liberti et al. |
| 5,925,573 A | 7/1999 | Colin et al. |
| 5,935,825 A | 8/1999 | Nishimura et al. |
| 5,948,412 A | 9/1999 | Murphy |
| 5,955,583 A | 9/1999 | Beavo et al. |
| 5,985,153 A | 11/1999 | Dolan et al. |
| 5,993,665 A | 11/1999 | Terstappen et al. |
| 6,013,188 A | 1/2000 | Terstappen et al. |
| 6,013,532 A | 1/2000 | Liberti et al. |
| 6,060,882 A | 5/2000 | Doty |
| 6,097,188 A | 8/2000 | Sweedler et al. |
| 6,100,099 A | 8/2000 | Gordon et al. |
| 6,120,856 A | 9/2000 | Liberti et al. |
| 6,136,182 A | 10/2000 | Dolan et al. |
| 6,138,077 A | 10/2000 | Brenner |
| 6,146,838 A | 11/2000 | Williams et al. |
| 6,150,516 A | 11/2000 | Brenner et al. |
| 6,172,214 B1 | 1/2001 | Brenner |
| 6,172,218 B1 | 1/2001 | Brenner |
| 6,194,900 B1 | 2/2001 | Freeman et al. |
| 6,228,624 B1 | 5/2001 | Terstappen |
| 6,235,475 B1 | 5/2001 | Brenner et al. |
| 6,236,205 B1 | 5/2001 | Ludeke et al. |
| 6,242,915 B1 | 6/2001 | Hurd |
| 6,265,150 B1 | 7/2001 | Terstappen et al. |
| 6,287,791 B1 | 9/2001 | Terstappen et al. |
| 6,307,372 B1 | 10/2001 | Sugarman et al. |
| 6,326,787 B1 | 12/2001 | Cowgill |
| 6,348,318 B1 | 2/2002 | Valkirs |
| 6,352,828 B1 | 3/2002 | Brenner |
| 6,361,749 B1 | 3/2002 | Terstappen et al. |
| 6,361,944 B1 | 3/2002 | Mirkin et al. |
| 6,365,362 B1 | 4/2002 | Terstappen et al. |
| 6,397,094 B1 | 5/2002 | Ludeke et al. |
| 6,404,193 B1 | 6/2002 | Dourdeville |
| 6,456,072 B1 | 9/2002 | Webb et al. |
| 6,469,636 B1 | 10/2002 | Baird et al. |
| 6,487,437 B1 | 11/2002 | Viswanathan et al. |
| 6,495,357 B1 | 12/2002 | Fuglsang et al. |
| 6,512,941 B1 | 1/2003 | Weiss et al. |
| 6,514,415 B2 | 2/2003 | Hatch et al. |
| 6,551,843 B1 | 4/2003 | Rao et al. |
| 6,555,324 B1 | 4/2003 | Olweus et al. |
| 6,582,938 B1 | 6/2003 | Su et al. |
| 6,587,706 B1 | 7/2003 | Viswanathan |
| 6,594,517 B1 | 7/2003 | Nevo |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,645,731 B2 | 11/2003 | Terstappen et al. |
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B1 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Hockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbic |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |

(56) References Cited

U.S. PATENT DOCUMENTS

| | | |
|---|---|---|
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2 | 9/2014 | Dryga et al. |
| 8,889,368 B2 | 11/2014 | Barbreau et al. |
| 9,389,225 B2 | 7/2016 | Dryga et al. |
| 9,434,940 B2 | 9/2016 | Dykes |
| 9,476,812 B2 | 10/2016 | Dryga et al. |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0098531 A1 | 7/2002 | Thacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |
| 2002/0164629 A1 | 11/2002 | Quake et al. |
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |
| 2003/0129676 A1 | 7/2003 | Terstappen et al. |
| 2003/0203507 A1 | 10/2003 | Liberti et al. |
| 2003/0206577 A1 | 11/2003 | Liberti et al. |
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. |
| 2006/0024756 A1 | 2/2006 | Tibbe et al. |
| 2006/0115380 A1 | 6/2006 | Kagan et al. |
| 2006/0129237 A1 | 6/2006 | Imran |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrell et al. |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0264629 A1 | 11/2007 | Holmes et al. |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0068723 A1 | 3/2010 | Jovanovich et al. |
| 2010/0072994 A1 | 3/2010 | Lee et al. |
| 2010/0129785 A1 | 5/2010 | Pris et al. |
| 2010/0137143 A1 | 6/2010 | Rothberg et al. |
| 2010/0144005 A1 | 6/2010 | Bin Kingombe et al. |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0098623 A1 | 4/2011 | Zhang et al. |
| 2011/0104718 A1 | 5/2011 | Rao et al. |
| 2011/0137018 A1 | 6/2011 | Chang-Yen et al. |
| 2011/0183398 A1 | 7/2011 | Dasaratha et al. |
| 2011/0262893 A1 | 10/2011 | Dryga et al. |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0300609 A1 | 12/2011 | Lim et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0100546 A1 | 4/2012 | Lowery, Jr. et al. |
| 2012/0112744 A1 | 5/2012 | McDowell et al. |
| 2013/0109590 A1 | 5/2013 | Clarizia et al. |
| 2013/0196341 A1 | 8/2013 | Neely et al. |
| 2013/0203634 A1 | 8/2013 | Jovanovich et al. |
| 2013/0316355 A1 | 11/2013 | Dryga et al. |
| 2014/0100136 A1 | 4/2014 | Clarizia et al. |

(56) References Cited

U.S. PATENT DOCUMENTS

| | | |
|---|---|---|
| 2014/0170021 A1 | 6/2014 | Dryga |
| 2014/0170639 A1 | 6/2014 | Norvell |
| 2014/0170640 A1 | 6/2014 | Dykes |
| 2014/0170641 A1 | 6/2014 | Macemon |
| 2014/0170652 A1 | 6/2014 | Sitdikov et al. |
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | |
|---|---|---|
| EP | 2261650 A2 | 12/2010 |
| WO | 1988/003957 A1 | 6/1988 |
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | 95/31481 A1 | 11/1995 |
| WO | 98/20148 A1 | 5/1998 |
| WO | 99/53320 A1 | 10/1999 |
| WO | 01/73460 A1 | 10/2001 |
| WO | 02/98364 A2 | 12/2002 |
| WO | 2005/026762 A1 | 3/2005 |
| WO | 2005106480 A1 | 11/2005 |
| WO | 2007/018601 A1 | 2/2007 |
| WO | 2007/123345 A1 | 11/2007 |
| WO | 2007/135099 A1 | 11/2007 |
| WO | 2007123342 A1 | 11/2007 |
| WO | 2008/119054 A1 | 10/2008 |
| WO | 2008/139419 A1 | 11/2008 |
| WO | 2009/048673 A2 | 4/2009 |
| WO | 2009/055587 A1 | 4/2009 |
| WO | 2009072003 A2 | 6/2009 |
| WO | 2009/122216 A1 | 10/2009 |
| WO | 2011/019874 A1 | 2/2011 |
| WO | 2011/133630 A1 | 10/2011 |
| WO | 2011/133632 A1 | 10/2011 |
| WO | 2011/133759 A1 | 10/2011 |
| WO | 2011/133760 A1 | 10/2011 |

OTHER PUBLICATIONS

Harkins and Harrigan, "Labeling of Bacterial Pathogens for Flow Cytometric Detection and Enumeration" Curr Prot Cytom (2004) 11.17.1-11.17.20.
Harlow, et al., 1988, 'Antibodies', Cold Spring Harbor Laboratory, pp. 93-117.
Harris et al., Science 320:106-109 (2008).
Heijnen et al., 2009, Method for rapid detection of viable *Escherichia coli* in water using real-time NASBA, Water Research, 43:3124-3132.
Hijmans, et al., An immunofluorescence procedure for the detection of intracellular immunoglobulins, Clin. Exp. Immunol., 4:457 (1969).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Hunter, et al., Immunoassays for Clinical Chemistry, pp. 147-162, Churchill Livingston, Edinborough (1983).
Inai, et al., Immunohistochemical detection of an enamel protein-related epitope in rat bone at an early stage of osteogenesis, Histochemistry, 99(5):335-362 (1993).
International Search Report for PCT/US2013/076649 with an International filing date Dec. 19, 2013, 2 pages.
International Search Report in PCT/US2011/33184, dated Jul. 25, 2011, 2 pages.
International Search Report in PCT/US2011/33186, dated Jun. 22, 2011, 1 page.
International Search Report in PCT/US2011/33410, dated Jul. 19, 2011, 2 pages.
International Search Report in PCT/US2011/33411, dated Jun. 22, 2011, 1 page.
International Search Report issued in PCT/US2013/076649, dated Feb. 27, 2014.
ISR and Written Opinion in PCT/US2008/058518, dated Sep. 29, 2009, 15 pages.
ISR and Written Opinion in PCT/US2008/058518, dated Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
ISR and Written Opinion in PCT/US2011/48447, dated Dec. 22, 2011, 7 pages.
ISR and Written Opinion in PCT/US2011/48452, dated Dec. 22, 2011, 7 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Klaschik, S., L. E. Lehmann, et al. (2002). "Real-time PCR for detection and differentiation of gram-positive and gram-negative bacteria." J Clin Microbiol 40(11): 4304-4307.
Lecomte et al. Nucl Acids Res. 11:7505 (1983).
Lee, et al., Chip-NRM Biosensor for detection and molecular analysis of cells, Nature Medicine, 14(8):869-874 (2008).
Levin, Cell 88:5-8 (1997).
Li et al., 2010, Chemiluminescent Detect of *E. coli* O157:H7 Using Immunological Method Based on Magnetic Nanoparticles, J. of Nanoscience and Nanotechnology 10:696-701.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Lu et al., 2007, Magnetic Nanoparticles: Synthesis, Protection, Functionalization, and Application, Angew. Chem. Int. Ed. 46:1222-1244.
Lund, et al., Immunomagnetic separation and DNA hybridization for detection of enterotoxigenic *Escherichia coli* in a piglet model, J. Clin. Microbiol., 29:2259-2262 (1991).
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John Wiley & Sons, GB, vol. 15, No. 13, Jan. 1, 2001, pp. 1068-1074.
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Margin, et al., High resolution microcoil 1H-NMR for mass-limited, nanoliter-volume samples, Science, 270:1967 (1995).
Margulies et al., Nature, 437: 376-380 (2005).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
Matar et al., 1990, Magnetic particles derived from iron nitride, IEEE Transactions on magnetics 26(1):60-62.
McDowell, et al., Operating Nanoliter Scale NMR Microcoils in a Itesla Field, J. Mag. Reson., 188(1):74-82 (2007).

(56) References Cited

OTHER PUBLICATIONS

Minard, et al., Solenoidal Microcoil Design, Part I: Optimizing RF Homogeneity and coil dimensions, Concepts in Magn. Reson., 13(2):128-142 (2001).

Moreira et al., 2008, Detection of *Salmonella typhimurium* in Raw Meats using In-House Prepared Monoclonal Antibody Coated Magnetic Beads and PCR Assay of the fimA Gene. Journal of Immunoassay & Immunochemistry 29:58-69.

Moresi and Magin, Miniature Permanent Magnet for Table-top NMR, Concept. Magn. Res., 19B:35-43 (2003).

Moudrianakis et al., Proc. Natl. Acad. Sci. 53:564-71 (1965).

Mulder, et al., Characterization of two human monoclonal antibodies reactive with HLA-B12 and HLA-B60, respectively, raised by in vitro secondary immunization of peripheral blood lymphocytes, Hum. Immunol., 36(3):186-192 (1993).

Myers and Gelfand, Biochemistry 30:7661 (1991).

Narang et al., Methods Enzymol., 68:90 (1979).

Agrawal et al., 1990, Tetrahedron Letters 31:1543-46.

Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.

Armenean, et al., NMR Radiofrequency Microcoil Design: Electromagnetic Simulation Usefulness, Compes Rendus Biologies, 325(4):457-463 (2002).

Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.

Barany et al., Gene, 108:1 (1991).

Barany F. (1991) PNAS 88:189-193.

Barany, F., Genome research, 1:5-16 (1991).

Behnia and Webb, Limited-Sample NMR Using Solenoidal Microcoils, Perfluorocarbon Plugs, and Capillary Spinning, Anal. Chem., 70:5326-5331 (1998).

Braslaysky et al., PNAS, 100:3690-3694 (2003).

Brown et al., Methods Enzymol., 68:109 (1979).

Bruno et al., "Development of an Immunomagnetic Assay System for Rapid Detection of Bacteria and Leukocytes in Body Fluids," J Mol Recog, 9 (1996) 474-479.

Burtis et al. (Burtis, C.A. (Ed.), Tietz Textbook of Clinical Chemistry, 3rd Edition (1999), W.B. Saunders Company, Philadelphia, PA, pp. 1793-1794).

Butter et al., 2002, Synthesis and properties of iron ferrofluids, J. Magn. Magn. Mater. 252:1-3.

Byrne, et al., Antibody-Based Sensors: Principles, Problems and Potential for Detection of Pathogens and Associated Toxins, Sensors, 9:4407-4445 (2009).

Campuzano, et al., Bacterial Isolation by Lectin Modified Microengines, Nano Lett. Jan. 11, 2012; 12(1): 396-401.

Cann et al., Proc. Natl. Acad. Sci. 95:14250 (1998).

Cariello et al., Nucl Acids Res, 19:4193 (1991).

Carroll, N. M., E. E. Jaeger, et al. (2000). "Detection of and discrimination between grampositive and gram-negative bacteria in intraocular samples by using nested PCR." J Clin 15 Microbiol 38(5): 1753-1757.

Chandler et al., Automated immunomagnetic separation and microarray detection of *E. coli* O157:H7 from poultry carcass rinse, Int. J. Food Micro., 70 (2001) 143-154.

Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).

Cheng et al, 2012, Concentration and detection of bacteria in virtual environmental samples based on non-immunomagnetic separation and quantum dots by using a laboratory-made system, Proc. of SPIE:82310Y-1-82310Y-18.

Chien et al., J. Bacterial, 127:1550 (1976).

Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.

Ciobanu and Pennington, 3D Micron-scale MRI of Single Biological Cells, Solid State Nucl. Magn. Reson., 25:138-141 (2004).

Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725.full?text_only=true on Mar. 9, 2015, one page.

Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.

Cross, et al., Choice of Bacteria in Animal Models of Sepsis, Infec. Immun. 61(7):2741-2747 (1983).

Dam et al. "Garlic (*Allium sativum*) Lectins Bind to High Mannose Oligosaccharide Chains", Journal of Biological Chemistry vol. 273, No. 10, Issue of Mar. 6, pp. 5528-5535, 1998.

Diaz et al., Braz J. Med. Res., 31:1239 (1998).

Djukovic, et al., Signal Enhancement in HPLC/Microcoil NMR Using Automated Column Trapping, Anal. Chem., 78:7154-7160 (2006).

Dover, Jason E., et al. "Recent advances in peptide probe-based biosensors for detection of infectious agents." Journal of microbiological methods 78.1 (2009): 10-19.

Drancourt, et al., Diagnosis of Mediterranean Spotted Fever by Indirect Immunofluorescence of Rickettsia conorii in circulating Endothelial Cells Isolated with Monoclonal Antibody-Coated Immunomagnetic Beads, J. Infectious Diseases, 166(3):660-663, 1992.

Dynabeads® for Immunoassay IVD, retrieved from http://www.invitrogen.com/site/i3s/en/home/Products-and-Services/Applications/DiagnosticsClinical-Research/Bead-based-IVD-Assays/Bead-based-Immunoassay-iVD.html on May 29, 2013, four pages).

Elnifro, Elfath M., et al."Multiplex PCR: optimization and application in diagnostic virology." Clinical Microbiology Reviews 13.4 (2000): 559-570.

Engvall, Enzyme immunoassay ELISA and EMIT, Meth. in Enzymol., 70:419-439 (1980).

Extended European Search Report issued in EP 11864030.9, dated Aug. 20, 2014.

Extended European Search Report, dated Oct. 15, 2013 for EP application No. 11772606.7.

Fan, et al., Self-assembly of ordered, robust, three-dimensional gold nanocrystal/silica arrays, Science, 304:567 (2004).

Fenwick et al., 1986, Mechanisms Involved in Protection Provided by Immunization against Core Lipopolysaccarides of *Escherichia coli* J5 from Lethal Haemophilus pleuropneumoniae Infections in Swine, Infection and Immunity 53 (2):298-304.

Fu, et al., Rapid Detection of *Escherichia coli* O157:H7 by Immunogmagnetic Separation and Real-time PCR, Int. J. Food Microbiology, 99(1):47-57, (2005).

Fung, M-C et al. PCR amplification of mRNA directly from a crude cell lysate prepared by thermophilic protease digestion, Nucleic Acids Research, vol. 19 (15), p. 4300, 1991.

Goding, J.W., Conjugation of antibodies with fluorochromes: modifications to the standard methods, J. Immunol. Meth., 13:215 (1976).

Goloshevsky, et al., Development of Low Field Nuclear Magnetic Resonance Microcoils, Rev. Sci. Inst . . . , 76:024101-1 to 024101-6 (2005).

Goloshevsky, et al., Integration of Biaxial Planar Gradient Coils and an RF Microcoil for NMR Flow Imaging, Meas. Sci. Technol., 16:505-512 (2005).

Grant, et al., Analysis of Multilayer Radio Frequency Microcoils for Nuclear Magnetic Resonance Spectroscopy, IEEE Trans. Magn., 37:2989-2998 (2001).

Grant, et al., NMR Spectroscopy of Single Neurons, Magn. Reson. Med., 44:19-22 (2000).

Griffiths et al., 1994, Isolation of high affinity human antibodies directly from large synthetic repertoires. EMBO J. 13 (14):3245-3260.

(56) References Cited

OTHER PUBLICATIONS

Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.
Halbach, Design of Permanent Multipole Magnets with Oriented Rare Earth Cobalt Material, Nuclear Instrum Methods, 169:1-10 (1980).
Nordstrom et al., J. Biol. Chem. 256:3112 (1981).
Nyquist, Thermal Agitation of Electrical Charge in Conductors, Phys. Rev., 32:110-113 (1928).
Ohno et al, 2011, Effects of Blood Group Antigen-Binding Adhesin Expression during Helicobacter pylori Infection of Mongolian Gerbils, The Journal of Infectious Diseases 203:726-735.
Olson, et al., High-resolution microcoil NMR for analysis of mass-limited, nanoliter samples, Anal. Chem., 70:645-650 (1998).
Olsvik_et_al_Magnetic_Seperation_Techniques_in_Diagnostic_Microbiology_Clinical_Microbiol_Rev_1994_7_43_54.
Pappas, et al., Cellular Separations: A Review of New Challenges in Analytical Chemistry, Analytica Chimica Acta, 601(1):26-35 (2007).
Payne, M.J. et al., "The Use of Immobilized Lectins in the Separation of *Staphylococcus aureus, Escherichia coli, Listeria* and *Salmonella* spp. from Pure Cultures and Foods", Journal of Applied Bacteriology, 1992, No. 73, pp. 11-52 (12 Pages).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Safarik et al., "The application of magnetic separations in applied Microbiology" Journal of Applied Bacteriology 1995, 78, 575-585.
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Sista et al., 2008, Heterogeneous Immunoassays Using Magnetic beads on a Digital Microfluidic Platform, Lab Chip 8 (2):2188-2196.
Skjerve, et al., Detection of Listeria monocytogenes in foods by immunomagnetic separation, Appl. Env. Microbiol., 56:3478 (1990).
Soni et al., Clin Chem 53:1996-2001 (2007).
Sorli, et al., Micro-spectrometer for NMR: analysis of small quantities in vitro, Meas. Sci. Technol., 15:877-880 (2004).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stocker, et al. Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Takagi et al., Appl. Environ. Microbiol. 63:4504 (1997).
Taktak, et al., Multiparameter Magnetic Relaxation Switch Assays, Analytical Chemistry, 79(23):8863-8869 (2007).
The United States Naval Research Laboratory (NRL), "The FABS Device: Magnetic Particles", retrieved from http://www.nrl.navy.mil/chemistry/6170/6177/beads.php on Jan. 8, 2013, two pages.
Torensama, et al. Monoclonal Antibodies Specific for the Phase-Variant O-Acetylated Ki Capsule of *Escerichia coli*, J. Clin. Microbiol., 29(7):1356-1358 (1991).
Trumbull, et al., Integrating microfabricated fluidic systems and NMR spectroscopy, IEEE Trans. Biomed. Eng., 47 (1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Vandeventer, J. Clin. Microbiol. Jul. 2011, 49(7):2533-39.
Venkateswaran, et al., Production of Anti-Fibroblast Growth Factor Receptor Monoclonal Antibodies by In Vitro Immunization, Hybridoma, 11(6):729-739 (1992).
Verma, Biochim Biophys Acta. 473:1-38 (1977).
Vermunt, et al., Isolation of *Salmonelas* by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Trade-offs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Yeung et al., 2002, Quantitative Screening of Yeast Surface-Displayed Polypeptide Libraries by Magnetic Bead Capture. Biotechnol. 18:212-220.
Yu et al. "Development of a Magnetic Microplate Chemifluorimmunoassay for Rapid Detection of Bacteria and Toxin in Blood", Analytical Biochemistry 261 (1998), pp. 1-7.
Zhao et al. A rapid bioassay for single bacterial cell quantitation using bioconjugated nanoparticles, PNAS, 101(42):15027-15032 (2004).
Zordan, et al. Detection of Pathogenic *E. coli* O157:H7 by a Hybrid Microfluidic SPR and Molecular Imaging Cytometry Device, Cytometry A, 75A:155-162 (2009).

METHODS FOR UNIVERSAL TARGET CAPTURE

RELATED APPLICATIONS

The present application is a continuation of U.S. patent application Ser. No. 14/107,335, filed Dec. 16, 2013, which is currently allowed and to be issued as U.S. Pat. No. 9,434,940, and which claims the benefit of and priority to U.S. provisional patent application Ser. No. 61/739,567, filed Dec. 19, 2012, the contents of each of which are incorporated by reference herein in their entirety.

FIELD OF THE INVENTION

The invention generally relates to methods for universal target capture.

BACKGROUND

Blood-borne pathogens are a significant healthcare problem. A delayed or improper diagnosis of bacterial infection can result in sepsis—a serious and sometimes deadly inflammatory response. Sepsis is among the ten leading causes of death in the United States. See Martin, et al., 2003, NEJM, 348:1546-1554. Exports report that sepsis causes more deaths per year than prostate cancer, breast cancer and HIV/AIDS combined and that sepsis is the most important cause of death in intensive care units.

Early detection of bacterial infections is the key to preventing the onset of sepsis. Traditional methods of detecting blood-borne infections include lab cultures that require days to complete. Other molecular methods of detecting bacteria require the bacteria to first be captured and the DNA isolated from the captured bacteria. Capturing the bacteria typically requires prior knowledge about the bacteria that is sought to be detected. That information is not always available, particularly when a patient comes to a healthcare facility having an unknown infection.

SUMMARY

The invention provides universal target capture methods. Methods of the invention involve introducing an agent to a sample that causes an unknown target in the sample to display a universally recognized element. Accordingly, any capture moiety that is able to bind to the element can be used to isolate the target from the sample, regardless of the type of target in the sample. Methods of the invention are particularly useful for isolating unknown microorganisms from a sample by causing the microorganisms to display a certain protein that is recognized by an antibody, so that the antibody can be used to capture the microorganism in the sample.

The invention provides methods and devices for isolating a target from a sample by introducing to the sample a binding element that is displayed on the target. The invention is especially useful in samples comprising multiple different targets, in which case the binding element is incorporated into all targets and presents a common binding element for isolation of all targets in the sample. In a preferred embodiment, the target is a pathogen or a plurality of pathogens. For example, if the pathogen is a bacterium, methods of the invention contemplate the introduction of a vector (e.g., a virus) to induce the expression of an antigen in the pathogen(s) for binding by, e.g., an antibody in order to facilitate isolation of the pathogen(s). Viruses capable of acting on a range of target pathogens allows a broad range of unknown pathogens to be discovered, detected, and/or isolated. A virus, a cocktail of different viruses, other agents such as plasmids or bacterial ghosts, or combinations thereof are useful to induce common attachment or expression of binding elements. The use of a virus or vector that attaches to a broad range of pathogens, causing display of a common binding element is one example of implementation of the invention. Thus, methods are provided that are useful for the early detection of bacterial infections with high sensitivity, even when pathogen identity is unknown. Methods of the invention allow early detection and characterization of an infection (e.g., a bacterial infection), thus reducing the incidence and impact of negative effects of the infection (e.g. sepsis).

In certain aspects, the invention provides methods of isolating pathogen in which a virus or preparation of viruses are introduced to a sample suspected of containing a pathogen. The virus or viral preparation is used to cause the pathogens to each present a binding element. Pathogens are then separated from the sample using a binding partner that is specific for the binding element. In one embodiment, the viral preparation contains one or more vectors or viruses such as a bacteriophage including, for example, a broad-host-range bacteriophage, a functionalized bacteriophage such as a biotinylated bacteriophage, a phasmid, a phagemid, a plasmid, or a bacterial ghost.

In one example, a bacteriophage transfects a bacterial pathogen and cause it to express a cell-surface antigen. Where phage transfection induces the pathogen to express a cell-surface antigen, the target-specific binding partner may include an antibody. In some embodiments, a bacteriophage displays a peptide on its capsid. Where the displayed peptide is an antigen, the target-specific binding partner may include an antibody. In certain embodiments, the peptide displayed on the bacteriophage capsid is biotinylated and the target-specific binding partner comprises avidin or streptavidin.

Target-specific binding elements include any member of a binding pair known in the art and capable of being expressed in a pathogen. Non-limiting examples include antibodies, biotin, avidin, streptavidin, carbohydrates, lectins, hormones, digoxigenin, anti-digoxigenin, and others. The binding partner may further include a solid substrate such as a bead, a surface, or a magnetic bead.

The binding element displayed on the target binds to the binding partner, for example, through antibody-antigen binding or through streptavidin-biotin binding. The binding partner can then be separated from the sample by exploiting the properties of a solid substrate. Where the solid substrate includes a fixed surface, such as a wall within a microfluidic channel or beads in a column, the sample can be washed out. Where the solid substrate includes magnetic beads, magnetic separation techniques may be used. For example, a magnet can be used to capture target/particle complexes and the excess sample washed away.

In other embodiments, a common binding partner is attached to pathogen in a sample via a binding element that is common to the pathogen class to be detected. Attachment chemistries are known in the art and depend upon the nature of the pathogen to be detected.

Methods of the invention are not limited to pathogen detection and can be used to detect any target in a sample. For example, methods of the invention are useful for detection of environmental targets in samples obtained, e.g., from soil, water and other elements in the environment. Common binding partners are introduced as described above or can be introduced by chemical attachment via a linker or other binding moiety. Methods of the invention are also useful for detection of biohazards in samples obtained in the environment or in samples suspected of containing biohazards introduced by humans (e.g., anthrax and the like).

Methods of the invention may be employed to separate two or more unknown pathogens from a sample when those pathogens are initially present in low concentrations. In some embodiments, one or both of the pathogens is present at a concentration beneath 1 CFU/mL of sample prior to separation. The separation may be performed using lab techniques such as affinity purification. In some embodiments, the separation is performed using a fluidic chip. Once separated, the pathogens may be cultured detected using a technique such as NMR, PCR, mass spectrometry, impedance measurement, visual detection, or other means.

DETAILED DESCRIPTION

The invention generally relates to methods and devices for extracting one or more targets from a sample by causing targets in the sample to present a common binding element. The target can then be isolated using a binding partner that specifically binds to the binding element; such as an antibody binding to an antigen or streptavidin binding to biotin, and others known in the art. In one embodiment, the binding element is attached to a substrate, enabling the sample to be washed, leaving behind the target to be detected. In a preferred embodiment, the targets are pathogens or environmental hazards.

Methods of the invention can involve using a magnetic particle as a substrate attached to a binding partner, thereby forming a target/magnetic particle complex. Methods of the invention can further involve applying a magnetic field to capture the target/magnetic complex on a surface and wash away the sample. The invention further provides devices for extracting the pathogens. Devices of the invention can involve fluidic channels and chambers having macrofluidic dimension, microfluidic dimensions, or both.

Figure 1:
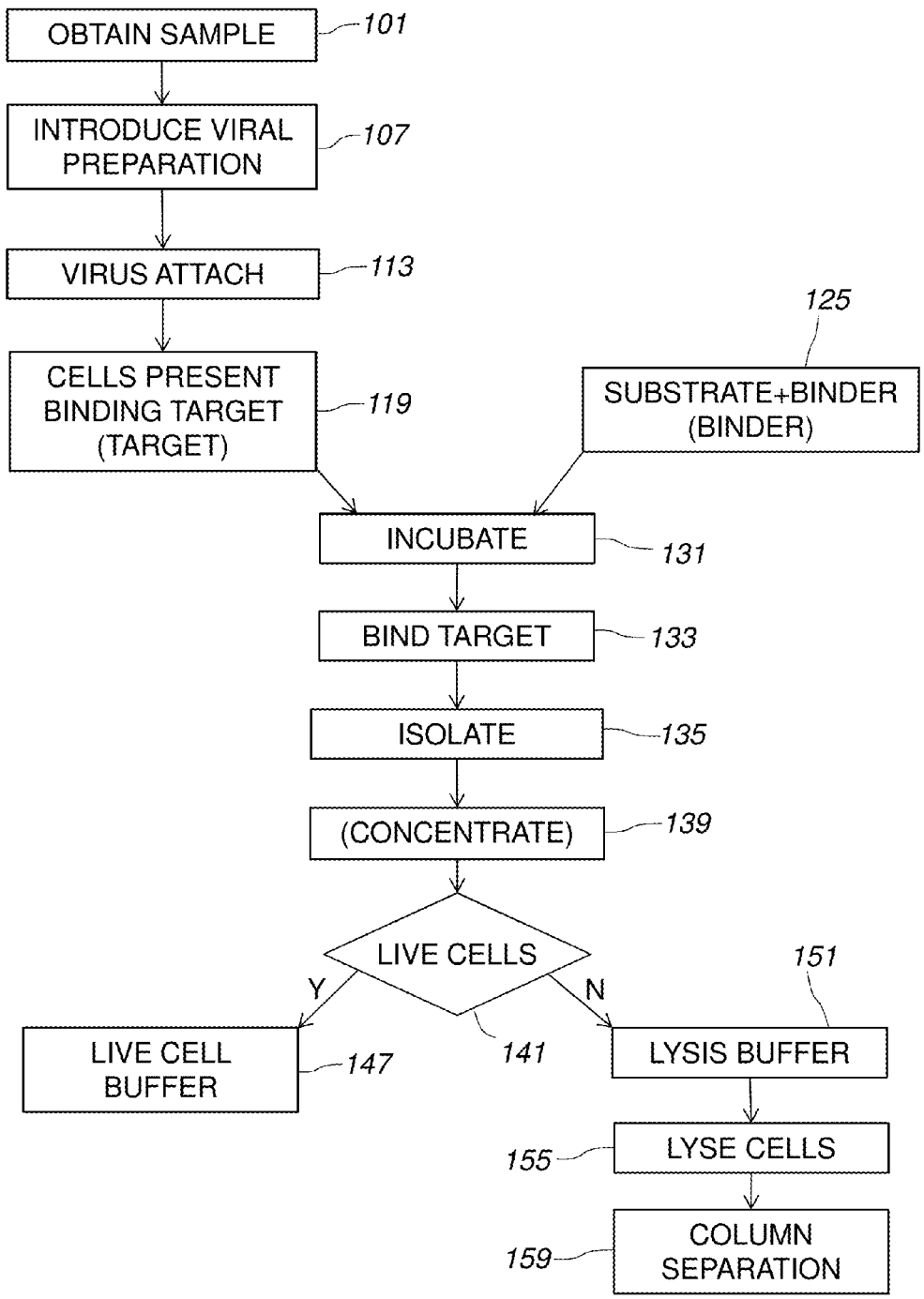
FIG. 1 gives a diagram of methods for isolating different pathogens.

FIG. 1 provides an exemplary diagram of certain methods for isolating different pathogens. A sample that contains two or more different pathogens is obtained 101. Methods of the invention may be used to isolate or extract different unknown pathogens from any heterogeneous sample. For example, the sample may include a bodily tissue or fluid. In particular embodiments, the sample is a bodily fluid. A bodily fluid refers to a liquid material derived from, for example, a human or other mammal. Such bodily fluids include, without limit, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A bodily fluid may also be a fine needle aspirate. A bodily fluid may also be media containing cells or biological material.

Methods of the invention are suitable for use with any type of sample including one or more different pathogens including unknown pathogens. The target pathogen refers to the substance in the sample that will be captured and isolated by methods of the invention. Other targets may be captured by methods and devices of the invention. The target may be bacteria, fungi, a protein, a cell (such as a cancer cell, a white blood cell, a virally infected cell, or a circulating fetal cell), a virus, a nucleic acid (e.g., DNA or RNA), a receptor, a ligand, a hormone, a drug, a chemical substance, or any molecule known in the art.

In certain aspects, the target pathogen is a bacterium or two or more different bacteria. Methods of devices of the invention can be used to isolate or extract known bacteria, unknown bacteria, or a combination thereof. Both gram positive bacteria, gram negative bacteria, archaea, or eukaryotes can be isolated using the methods disclosed herein. Specific genera of pathogens that may be sought and assayed for using the disclosed methods include *Alphaproteobacteria, Bacillus, Betaproteobacteria, Bifidobacterium, Borrelia, Campylobacter, Candida, Citrobacter, Clostridium, Enterobacter, Enterococcus, Escherichia, Flavobacterium, Fusobacterium, Gammaproteobacteria, Klebsiella, Kluyvera, Lactobacillus, Legionella, Leuconostoc, Listeria, Micrococcus, Mycobacterium, Neisseriaceae, Pediococcus, Pneumococcus, Porphyromonas, Prevotella, Propionibacterium, Proteus, Rhodospirillum, Rickettsia, Saccharomyces, Salmonella, Serratia, Shigella, Sphaerotilus, Staphylococcus, Streptococcus, Thermoanaerobacter, Thermoproteus, Vibrio,* and *Yersinia.*

Organisms that can be assayed for with methods and devices of the invention include *Acinetobacter calcoaceticus, Aeromonas hydrophila, Bacillus anthracis, Bacillus subtilis, Candida albicans, Citrobacter freundii, E. coli, Enterobacter aerogenes, Enterobacter cloacae, Enterococcus faecium, Fusobacterium nucleatum, Klebsiella oxytoca, Klebsiella pneumoniae, Klebsiella travesanii, Kluyvera ascorbata, Lactobacillus casei, Lactobacillus cellobiosus, Lactobacillus fermentum, Lactobacillus helveticus, Lactobacillus paracasei, Lactobacillus salivarius, Listeria monocytogenes, Micrococcus luteus, Pediococcus parvulus, Porphyromonas gingivalis, Prevotella intermedia, Propionibacterium freudenreichii, Proteus vulgaris, Pseudomonas aeruginosa, Rhodospirillum rubrum, Rickettsia conorii, Saccharomyces cerevsiae, Salmonella agona, Salmonella enteritidis, Salmonella heidelberg, Salmonella infantis, Salmonella minnesota, Salmonella montevideo, Salmonella ohio, Salmonella typhimurium, Serratia marcescens, Shigella flexneri, Sphaerotilus natans, Staphylococcus aureus, Staphylococcus epidermis, Staphylococcus xylosus, Streptococcus faecalis, Streptococcus pyrogenes, Thermoproteus tenax, Vibrio cholerae,* and *Yersinia pseudotuberculosis.* Any combination of organisms may be the target of methods and devices of the invention and the target of an assay will vary depending on the suspected pathogen or pathogens to be isolated.

In particular embodiments, the sample is a blood sample. Methods of the invention allow for different unknown pathogens in a blood sample to be isolated and detected at a level as low as or even lower than 1 CFU/ml. Blood may be collected in a container, such as the blood collection tube sold under the trademark VACUTAINER by BD (Franklin Lakes, N.J.). In certain embodiments, a solution is added that prevents or reduces aggregation of endogenous aggregating factors, such as heparin in the case of blood. A particular advantage of the methods described herein is the ability to capture and isolate different unknown pathogens directly from blood samples at low concentrations that are characteristic of clinical samples (as low as 1 CFU/ml of bacteria in a blood sample).

As shown in FIG. 1, once the sample is obtained 101, a viral preparation is introduced 107 into the sample. The viral preparation includes at least one virus that attaches 113 to the pathogens. As a result, the pathogens present 119 a binding element.

Any viral preparation may be used that causes different unknown pathogens to present a binding element. In some embodiments, the viral preparation contains a cocktail of bacteriophage. The cocktail contains different phage viruses that infect different bacteria. In certain embodiments, a broad-host-range phage is used that can infect different bacteria.

Phages are viruses that can be used as a transduction vector to introduce genetic material into the different pathogens and induce expression of, for example, a common antigen. Phage can be used as transduction vectors to introduce exogenous (non-viral) genetic material into the pathogens. See U.S. Pat. No. 7,148,054 for discussion. During lytic infection with a phage, DNA is packaged into phage heads as phage particles are formed. Promiscuous high-transducing (HT) mutants of P22 which efficiently package DNA with little sequence specificity are known.

As diagrammed in FIG. 1, infection involves attachment 113 of the phage particle to a target cell. When transduction is successful, the exogenous DNA is received in the target cell and expressed 119. For example, RecA-mediated homologous recombination following injection of the donor fragment can result in the inheritance of donor traits.

Any suitable phage or combination of phages can be used in methods of the invention. Examples of transducing phage vectors include bacteriophages P1 and P22 of *E. coli* and *S. typhimurium*, respectively. Other phages are suitable for use with methods of the invention. For example, the bacteriophage Mu can be used to insert DNA into a target pathogen genome for expression 119. See Groisman, 1991, In vivo genetic engineering with bacteriophage Mu, Methods in Enzymology 202:180-212. Further, hybrid phages such as Mud-P22 may be used. Mud-P22 is a hybrid combining features of phage Mu and P22. Mud-P22 can be inserted at essentially any desired site on the *Salmonella* chromosome. See Crain, 2007, Mud-P22, Methods Enzymology 421:249-59. Other exemplary phages (and their targets) include T4 (*E. coli*), T5 (*E. coli*), λ phage (*E. coli*), T7 phage (*E. coli*), G4 (*E. coli*), P1 (*E. coli*), ϕ6 (*Pseudomonas*), *Thermoproteus tenax* virus 1 (*Thermoproteus tenax*), M13 (*E. coli*), MS2 (*E. coli*), Qβ (*E. coli*), ϕX174 (*E. coli*), Φ29 (*Bacillus*), PZA (*Bacillus*), Φ15 (*Bacillus*), BS32 (*Bacillus*), B103 (*Bacillus*), M2Y (M2) (*Bacillus*), Nf (*Bacillus*), GA-1 (*Bacillus*), FWLBc1 (*Bacillus*), FWLBc2 (*Bacillus*), FWLLm3 (*Listeria*), B4 (*Propionibacterium*).

Phages are discussed in Chopin, et al., 2002, J Bact 184(7):2030-2033; Muramatsu et al., 1991, Two generalized transducing phages in *Vibrio parahaemolyticus* and *Vibrio alginolyticus*, Microbiol Immunol 35(12): 1073-1084; Regue et al., 1991, A generalized transducing bacteriophage for *Serratia marcescens*, Res Microbiol 42(1):23-27; Kiesel et al., 1993, Phage Acm1-mediated transduction in the facultatively methanol-utilizing *Acetobacter methanolicus* MB 58/4, J. Gen Virol 74(9):1741-1745; Zhang, et al., 2012, Food Microbiol 31(1):133-36; U.S. Pat. No. 7,732,150; U.S. Pub. 2009/0246752; U.S. Pub. 2009/0047254; and U.S. Pub. 2004/0156831, the contents of each of which are incorporated by reference.

Exemplary phages are further discussed in Welker, 1988, Transduction in *Bacillus stearothermophilus*, J. Bacteriol, 176(11):3354-3359; Darzins et al., 1989, Mini-D3112 bacteriophage transposable elements for genetic analysis of *Pseudomonas aeruginosa*, J. Bacteriol 171(7):3909-3916; Blahova et al., 1994, Transduction or imipenem resistance by the phage F-116 from a nosocomial strain of *Pseudomonas aeruginosa* isolated in Slovakia, Acta Virol 38(5):247-250; Weiss et al., 1994, Isolation and characterization of a generalized transducing phage for *Xanthomonas campestris* pv. *campestris*, J. Bacteriol 176(11): 3354-3359; Schicklmaier et al., 1995, Frequency of generalized transducing phages in natural isolates of the *Salmonella typhimurium* complex, Appl Environ Microbiol 61(4): 61(4): 1637-1640; Humphrey et al., 1997, Purification and characterization of VSH-1, a generalized transducing bacteriophage of *Serpulina hyodysenteriae*, J Bacteriol 179(2):323-329; Willi et a., 1997, Transduction of antibiotic resistance markers among *Actinobacillus actinomycetemcomitans* strains by temperate bacteriophages Aa phi 23, Cell Mol Life Sci 53(11-12):904-910; Nedelmann et al., 1998, Generalized transduction for genetic linkage analysis and transfer of transposon insertions in different *Staphylococcus epidermidis* strains, Zentiviralalbl Bakteriol 287(1-2):85-92; Int. Pat. Application Pub. WO 2003/035889; U.S. Pat. Nos. 8,071,337 and 7,951,579.

Any suitable phage virus or viruses, including any of those mentioned herein, can be included in the viral preparation. A viral preparation according to the invention is a composition containing a vector or viral material with the ability to interact with one or more different targets. A broad-host-range can be provided by including a cocktail of phages (e.g., two or more of any phage such as those mentioned herein), a phage that infects a range of hosts, or a combination thereof.

Any suitable broad-host-range phage can be used. For example, phage SN-1, SN-2, SN-X, SN-T, BHR1, BHR2, BHR3, BHR4, BHR5, PRD1, KVP40, PY100, PRD1, PVP-SE1, or a combination thereof may be included in a viral preparation. Broad host range phages are discussed in Miller et al., 2003, Complete genome sequence of the broad-host-range vibriophage KVP40: comparative genomics of a T4-related bacteriophage; J Bact 185(17):5220-5233; Beumer, 2005, A broad-host-range, generalized transducing phage SN-T acquires 16S rRNA genes from different genera of bacteria, Appl Env Microb 71(12):8301-8304; Green et al., 1985, Isolation and preliminary characterization of lytic and lysogenic phages with wide host range within the streptomycetes, J. Gen Microbiol 131(9):2459-2465; Jensen et al., 1998, Prevalence of broad-host-range lytic bacteriophages of *Sphaerotilus natans, Escherichia coli*, and *Pseudomonas aeruginosa*, Appl Environ Microbiol 64(2): 575-580; Bamford et al., 1995, Bacteriophage PRD1: a broad host range dsDNA tectivirus with an internal membrane, Adv Virus Res 45:281-319; Schwudke, et al., 2008, Broad-host-range *Yersinia* phage PY100: genome sequence, proteome analysis of virions, and DNA packaging strategy, J Bact 190(1):332-342; Olsen et al., 1974, Characteristics of PRD1, a plasmid-dependent broad host range DNA bacteriophage, J Viriol 14(3):689-699; Santos et al., 2011, Genomic and proteomic characterization of the broad host range *Salmonella* phage PVP-SE1: creation of a new phage genus, J Viriol 85(21):11265-73; Sillankorva et al., Efficacy of a broad host range lytic bacteriophage against *E. coli* adhered to urothelium, Curr Microbiol 62(4):1128-1132;

Evans et al, 2010, Characterization of a broad-host-range flagellum-dependent phage that mediates high-efficiency generalized transduction in, and between, *Serratia* and *Pantoea*, Microbiol 156:240-247; Garbe et al., 2010, Characterization of JG024, a *Pseudomonas aeruginosa* PB1-like broad-host range phage under simulated infection conditions, BMC Microbiol 10:301; Schwarzer et al., 2012, A multivalent adsorption apparatus explains the broad host range of phage phi92: a comprehensive genomic and structural analysis, J Viriol JVI.00801-12; U.S. Pub. 2012/0168372; U.S. Pub. 2012/0128652; and U.S. Pub. 2011/0064699, the contents of which are incorporated by reference.

A broad-host-range viral preparation can be provided by including more than one phage in the composition. For example, if each included phage is specific for one species, the phage cocktail will have the ability to infect multiple species. Any number of different phages (e.g., 3, 5, tens, hundreds) may be included in a phage cocktail. Those phages may themselves be narrow or broad in host range. Phage cocktails are discussed in Kelly et al., 2011, Development of a broad-host-range phage cocktail for biocontrol, Bioengineered Bugs 2:1, 31-37; Int. Application Pub. WO 02/07742; U.S. Pat. No. 6,121,036; U.S. Pub. 2009/0047254; and U.S. Pub. 2005/0032036, the contents of which are hereby incorporated by reference.

Other vectors may be used to cause different unknown pathogens to present a common binding element. Suitable vectors include plasmids, phagemids, and bacterial ghosts. In some embodiments, a plasmid is included, optionally enveloped in a lipid layer (e.g., a liposome, micelle, or reverse micelle), bi-layer, or a protein coat. Suitable plasmids are known in the art and include Col E1, RSF1030, clo DF13, R6K, F, R1, and Ent P 307.

In certain embodiments, one or more of the pathogens are targeted using a bacterial ghost. Bacterial ghosts are bacterial cell envelopes devoid of cytoplasmic content. A bacterial ghost can be included that exhibits one or more cell surface moieties that bind to any number of cell-surface targets on one or a range of bacteria. Further, the bacterial ghosts may each include the known common binding element (e.g., common antigen, biotinylated protein, streptavidin, etc.). Bacterial ghosts may be preferred since they can carry multiple surface moieties due to their size and are non-pathogenic themselves due to inactivity and can be stored (e.g., on-chip) for long periods of time. Bacterial ghosts are discussed in Lubitz et al., 2009, Applications of bacterial ghosts in biomedicine, Adv Exp Med Biol 655: 159-70; Langemann et al., 2010, The bacterial ghost platform system: production and applications, Bioeng Bugs 1(5):326-36; Tabrizi et al., 2004, Bacterial ghosts-biological particles as delivery systems for antigens, nucleic acids, and drugs, Curr Opp Biotechnol 15:530-537; U.S. Pat. Nos. 7,067,639; 6,896,887; U.S. Pub. 2012/0040829; and U.S. Pub. 2010/0203082, the contents of which are incorporated by reference for all purposes.

Preferably, the viral preparation is introduced 107 with a high concentration of phage or vector so that viruses attach 113 to all target pathogens. Viral preparations can further include additional components to facilitate transduction by, for example, contributing to the competency of the target cells to receive extrinsic genetic material or to inhibit infection or lysis by sources other than the phage vector or vectors used. Preparations may include one or more salt, buffer, chelator, ion, or combination thereof, in any suitable concentration. Infectious, non-transducing phage can be inhibited by ion chelators (e.g., citrate or EGTA). In some embodiments, bacterial nutrients are added to the viral preparation to encourage cell vitality. For example, trypticase soy or a sugar can be included.

As shown in FIG. 1, a binding partner, optionally bound to a substrate, is obtained 125 and introduced into the sample. The sample with the binding partner is incubated 131 so that the binding partner can bind 133 to the binding element on the pathogens. In some embodiments, the virus or vector is used to cause different pathogens to present different binding elements. The pathogens may then be extracted using different binding partners. For example, phages can be used that cause some bacteria to express antigen A, some to express antigen B, and so on. Substrate 219, such as magnetic beads, can then be used that include anti-A, anti-B, etc., antibodies bound to the surface. The different binding partners may be mixed on each substrate, or separated (e.g., some beads specific for antigen A and some for antigen B). This can facilitate downstream sorting (e.g., where magnetic meads have different magnetic strengths or other sortable properties). Once the pathogens are bound to the binding partner, the pathogens can be isolated 135 from the remainder of the sample. Methods are provided to optionally concentrate 139 the isolated pathogens. Isolation and concentration are discussed below.

The isolated pathogens may be handled according to whether isolated live cells or another product is intended 141. For live cells, the pathogens may be introduced 147 into a live cell buffer. Any other suitable detection or isolation may be performed. For example, where a product from the cells is desired, a lysis buffer may be introduced 151 to lyse 155 the cells. The lysate may be purified, extracted, separated, or similar. In some embodiments, DNA is extracted by separation 159 on a column.

Methods of the invention include using a viral preparation to cause the target pathogens to present 119 a binding element. Any suitable method of associating a pathogen with a binding element may be used with the invention. Suitable methods include expression of a cell-surface protein, phage display of a protein, or any other method of exposing a protein. A protein can be a binding element such as antigen or a protein can be further functionalized to present a binding element. For example, a protein can include a target for biotinylation and can be biotinylated such that biotin is a binding element and streptavidin can be used as a binding partner.

Figure 2:
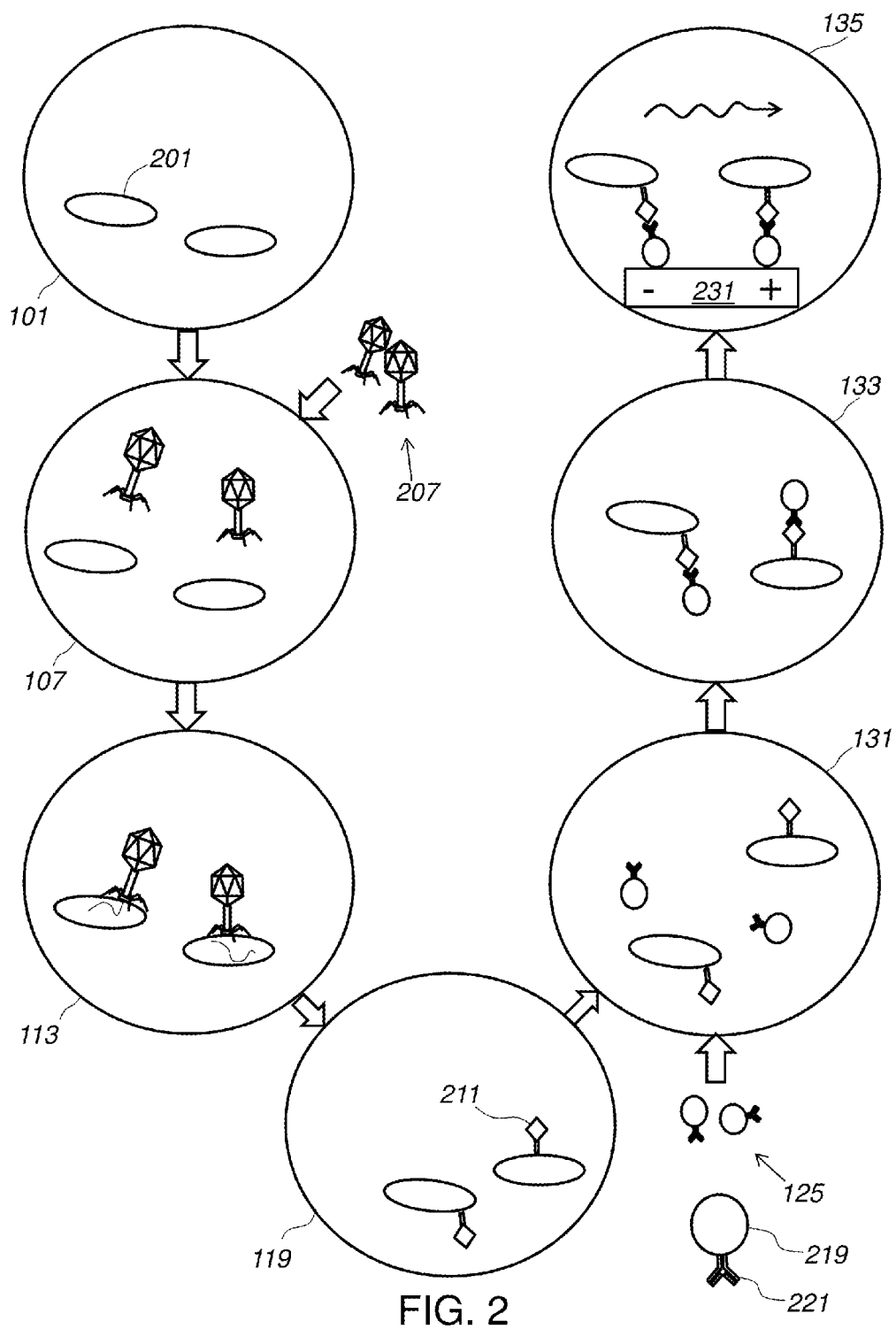
FIG. 2 illustrates inducing the expression of a common antigen by a viral preparation.

FIG. 2 illustrates the use of a viral preparation 207 to induce the expression of a common antigen 211 according to certain embodiments. As shown in FIG. 2, a sample containing unknown pathogens 201 is obtained 101 and viral preparation 207 is introduced 107. Viruses attach 113 to pathogens 201 and introduce exogenous DNA into those cells.

Phage viruses, such as any suitable one of those discussed herein, can be engineered to contain a gene for a common antigen 211 such as a cell surface protein. The phage or phages from viral preparation 207 inject the gene into pathogens 201. Pathogens 201 then express the gene causing them to present 119 antigen 211 on their cell surface. Engineering a gene into a phage vector is discussed in Green and Sambrook, 2012, Molecular Cloning: A Laboratory Manual 4Ed, Cold Spring Harbor Laboratory Press (Cold Spring Harbor, N.Y.), 2,000 pages and Primrose and Twyman, 2006, Principles of Gene Manipulation and Genomics, 7th Edition, Wiley-Blackwell (Malden, Mass.) 672 pages. Induction of antigen expression is discussed in Prisco and Berardinis, 2012, Filamentous bacteriophage Fd as an antigen delivery system in vaccination, Int J. Mol. Sci. 13:5179-

5194 and Gahan et al., 2009, Bacterial antigen expression is an important component in inducing an immune response to orally administered *Salmonella*-delivered DNA vaccines, PLoS One 4(6):e6062.

Antibody 221 may be obtained for use as the binding partner 125. As shown in FIG. 2, antibody 221 is bound to substrate 219. Substrate 219 can be any suitable substrate known in the art. In some embodiments, substrate 219 is the surface of a fluidic channel or other vessel. In some embodiments, substrate 219 is a biomolecule, such as a oligonucleotide, a protein, an aptamer, biotin, or some other such moiety that itself, in turn, has affinity for another material. For example, substrate 219 can be a DNA or RNA sequence, optionally with one or more locked nucleic acid (LNA) bases therein, and can be captured by exposure to a complementary sequence, such as a primer or oligo fixed on a glass slide or within a well in a microtitre plate. In certain embodiments, substrate 219 is a magnetic bead.

With continued reference to FIG. 2, the binding partner (e.g., antibody 221) is introduced into the vessel containing cells 201 expressing cell-surface antigen 211 and incubated 131. Incubation of antibody-bead complexes with cells 201 leads to binding 133 of substrate 219 to cells 201. Cells 201 can then be isolated 135 from the sample. Where substrate 219 is a surface of a vessel or channel, or a surface of beads packed into a column or otherwise held in place, cells 201 can be isolated 135 by using a wash solution to wash away excess sample. Where substrate 219 is a magnetic bead, a magnet 231 can then be used to isolate 135 cells 201 from the remainder of the sample.

Magnetic materials may be bound to target entities and used to separate such entities through the use of magnet fields and gradients. Magnetic materials and separations are known in the art and have been previously described, for example, in Murphy, 2011, Janeway's Immunobiology 8 Ed, Garland Science (New York, N.Y.), 888 pages, the contents of which are incorporated by reference herein. Methods of producing suitable magnetic particles are known in the art. See for example U.S. Pat. Nos. 5,597,531; 4,230,685; 4,677,055; 4,695,393; 5,695,946; 4,018,886; 4,267,234; 4,452,773; 4,554,088; 4,659,678; 5,186,827; 4,795,698, the contents of each of which are incorporated by reference.

Any type of magnetic particle may be used for substrate 219 in accordance with the invention. Methods of the invention include use of diamagnetic materials, paramagnetic materials, superparamagnetic materials, ferromagnetic materials, or a combination thereof (independently or in combination). Diamagnetic materials are slightly repelled by a magnetic field and the material does not retain the magnetic properties when the external field is removed. Paramagnetic materials (e.g., aluminum or platinum) are slightly attracted by a magnetic field and the material does not retain the magnetic properties when the external field is removed. Superparamagnetic materials are much more susceptible to magnetization than paramagnetic materials. See Gittleman et al., 1974, Superparamagnetism and relaxation effects in granular Ni—$SiO_2$ and Ni—$Al_2O_3$ films, Phys Rev B 9:3891-3897. Ferromagnetic materials (e.g., iron or nickel) exhibit a strong attraction to magnetic fields and are able to retain their magnetic properties after the external field has been removed.

Further, magnetic properties of substrate 219 may depend on the size of the particles of substrate. Some ferromagnetic materials, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic particles. In certain embodiments, the magnetic particle is an iron containing magnetic particle. In other embodiments, the magnetic particle includes iron oxide or iron platinum.

In some embodiments, the magnetic particles for substrate 219 include a portion of superparamagnetic particles by weight (e.g., 20%, 40%, 60%, or 80%). Particles 219 can have a diameter between about 100 nm and about 1,000 nm. In a particular embodiment, substrate 219 includes superparamagnetic particles of diameter between about 100 nm and about 250 nm. See discussion in U.S. Pub. 2011/0262989, the contents of which are incorporated by reference.

In certain embodiments, the particles are particles (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue particle aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the particles. It may also be advantageous to have the volumetric loading in a particle be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 tesla (T).

The size of the nanometal-containing particle may be optimized for a particular application, for example, maximizing moment loaded upon a target, maximizing the number of particles 219 on a target 201 with an acceptable detectability, maximizing desired force-induced motion, and/or maximizing the difference in attached moment between the labeled target and non-specifically bound targets or particle aggregates or individual particles. While maximizing is referenced by example above, other optimizations or alterations are contemplated, such as minimizing or otherwise desirably affecting conditions.

In an exemplary embodiment, a polymer particle containing 80 wt % $Fe_3O_4$ superparamagnetic particles, or for example, 90 wt % or higher superparamagnetic particles, is produced by encapsulating superparamagnetic particles with a polymer coating to produce a particle having a diameter of about 250 nm.

Each set of magnetic particles 219 has a binding partner 221 that allows for each set to specifically bind 133 the target 201 of interest in the sample. The binding partner may be any molecule known in the art and will depend on the target to be captured and isolated. Exemplary binding partners include nucleic acids, proteins, ligands, antibodies, aptamers, and receptors.

In particular embodiments, the binding partner 221 is an antibody, such as an antibody that binds a particular antigen 211 (see, e.g., FIG. 2). General methodologies for antibody production, including criteria to be considered when choosing an animal for the production of antisera, are described in Kontermann, 2010, Antibody Engineering Volume 1 2Ed, Springer-Verlag (Berlin Heidelberg) 800 pages, and Harlow, 1988, Antibodies: A Laboratory Manual, Cold Spring Harbor Laboratory Press (Cold Spring Harbor, N.Y.) 726 pages. For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant. Additional doses are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Such techniques are known in the art. See, e.g., Mulder et al., 1993, Characterization of two human monoclonal antibodies reactive with HLA-B12 and HLA-B60, respectively, raised by in vitro secondary immunization of peripheral blood lymphocytes, Hum. Immunol 36(3):186-192; Stauber et al., 1993, Rapid generation of monoclonal antibody-secreting hybridomas against African horse sickness virus by in vitro immunization and the fusion/cloning technique, J Immunol Methods 161(2):157-168; and Venkateswaran, et al., 1992, Production of anti-fibroblast growth factor receptor monoclonal antibodies by in vitro immunization, Hybridoma, 11(6):729-739. These techniques can be used to produce antigen-reactive monoclonal antibodies, including antigen-specific IgG, and IgM monoclonal antibodies.

Any antibody or fragment thereof having affinity and specific for the target of interest may be used for binding partner 221 within the scope of the invention provided herein.

Methods for attaching the binding partner 221 to the magnetic particle 219, including the coating of particles with antibodies, are known in the art. See for example Kontermann, 2010, Antibody Engineering Volume 1 2Ed, Springer-Verlag (Berlin Heidelberg) 800 pages; Harlow, 1988, Antibodies: A Laboratory Manual, Cold Spring Harbor Laboratory Press (Cold Spring Harbor, N.Y.) 726 pages; and Stanley, 2002, Essentials in Immunology and Serology, Delmar Cengage (Independence, Ky.) 560 pages. Such methodology can easily be modified by one of skill in the art to bind other types of binding partners to the magnetic particles. In addition, certain types of magnetic particles coated with a functional moiety are commercially available from Sigma-Aldrich (St. Louis, Mo.).

In some embodiments, more than one antibody 221 is used to create sets of magnetic particles. Since each set of particles 219 may be conjugated with antibodies 221 having different specificities for one or more antigen 211 coded in the genome of the phage or phages, compositions and concentrations may be optimized for detection of multiple unknown pathogens in the sample. In certain embodiments, all of the sets are provided at the same concentration. Alternatively, the sets are provided at different concentrations. For example, compositions may be designed such that sets that bind gram positive bacteria (e.g., antibody 221 to antigen 211 in genome of phage that targets Gram + cells 201) are added to the sample at a concentration of $2 \times 10^9$ particles per/ml, while sets that bind gram negative bacteria (e.g., antibody to antigen in genome of phage specific to Gram −) are added to the sample at a concentration of $4 \times 10^9$ particles per/ml. Compositions used with methods of the invention are not affected by antibody cross-reactivity. However, in certain embodiments, sets are specifically designed such that there is no cross-reactivity between different antibodies and different sets.

To facilitate downstream detection of pathogens 201, one or more labels may be added to antibody 221, particle 219, or both. For example, a label may be added during preparation of antibody/bead complexes. Any detectable label may be used with compositions of the invention, such as fluorescent labels, radiolabels, enzymatic labels, and others. The detectable label may be directly or indirectly detectable. In certain embodiments, the exact label may be selected based, at least in part, on the particular type of detection method used. Exemplary detection methods include radioactive detection, optical absorbance detection (e.g., UV-visible absorbance detection, optical emission detection, e.g., fluorescence, phosphorescence, chemiluminescence), or Raman scattering. Preferred labels include optically-detectable labels, such as fluorescent labels. Examples of fluorescent labels include without limit acridine and derivatives; BODIPY; Brilliant Yellow; coumarin and derivatives; DABITC; eosin and derivatives; erythrosin and derivatives; isothiocyanate; ethidium; fluorescein and derivatives; FAM; DTAF; QFITC, (XRITC); Malachite Green isothiocyanate; Phenol Red; pyrene and derivatives; Reactive Red 4 (Brilliant Red 3B-A sold under the trademark CIBACRON); rhodamine and derivatives; Texas Red; TAMRA; TRITC; riboflavin; Atto dyes; La Jolta Blue; phthalo cyanine; and naphthalo cyanine. Preferred labels include cyanine-3 and cyanine-5. Labels other than fluorescent labels are contemplated by the invention, including other optically-detectable labels. Methods of linking fluorescent labels to magnetic particles or antibodies are known in the art. Suitable labels and methods of their use are described in U.S. Pub. 2011/0262926, the contents of which are hereby incorporated by reference.

As shown in FIG. 2, the magnetic particles described above are then introduced 125 to the sample in order to bind 133 to the unknown pathogens 201. For example, a blood sample may be mixed with the described magnetic particles to generate a mixture that is allowed to incubate 131 such that the compositions bind to at least one pathogen 201 in the blood sample. The mixture is allowed to incubate 131 for a sufficient time to allow for the composition to bind to the pathogen in the blood. The process of binding the composition to the pathogen associates a magnetic moment with the pathogen, and thus allows the pathogen to be manipulated through forces generated by magnetic fields upon the attached magnetic moment.

In general, time for incubation 131 will depend on the desired degree of binding between the pathogen and the compositions of the invention (e.g., the amount of moment that would be desirably attached to the pathogen), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between about 5° C. and about 65° C., e.g., between about 15° C. and about 40° C.

In certain embodiments, a buffer solution is added to the sample along with the compositions of the invention. An exemplary buffer includes Tris(hydroxymethyl)-aminomethane hydrochloride (Tris HCl) at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in methods of the invention are designed to prevent lysis of blood cells, facilitate efficient binding of targets with magnetic particles and to reduce formation of particle aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic particle through ionic interaction. Tris HCl is frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining the integrity of blood cells.

Additional compounds can be used to modulate the capture efficiency by blocking or reducing non-specific interaction with blood components and either magnetic particles or pathogens. For example, chelating compounds, such as EDTA or EGTA, can be used to prevent or minimize interactions that are sensitive to the presence of $Ca^{2+}$ or $Mg^{2+}$ ions.

One can also use a static mixer or other mixing device that provides efficient mixing of viscous samples at high flow rates to achieve high binding efficiency while reducing time required for the binding step. In one embodiment, the sample is mixed with binding buffer in ratio of, or about, 1:1, using a mixing interface connector. The diluted sample then flows through a mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing.

With reference to FIG. 2, after binding 133 of particles 219 to pathogens 201 in the sample to form pathogen/magnetic particle complexes, a magnetic field 231 may be applied to the mixture to capture or isolate 135 the complexes on a surface. Components of the mixture that are not bound to magnetic particles will not be affected by the magnetic field and will remain free in the mixture. Methods and apparatuses for separating 135 target/magnetic particle complexes from other components of a mixture are known in the art. For example, a steel mesh may be coupled to a magnet, a linear channel or channels may be configured with adjacent magnets, or quadrapole magnets with annular flow may be used. Other methods and apparatuses for separating target/magnetic particle complexes from other components of a mixture are shown in U.S. Pat. Nos. 7,699,979; 6,551,843; 5,622,831; 6,514,415; 5,695,946; 5,186,827; 5,541,072; 5,466,574; and 6,623,983, the contents of each of which are incorporated by reference.

In certain embodiments, the magnetic capture is achieved at high efficiency by utilizing a flow-through capture cell with a number of strong rare earth bar magnets 231 placed perpendicular to the flow of the sample. When using a flow chamber with flow path cross-section 0.5 mm×20 mm (h×w) and 7 bar NdFeB magnets, the flow rate could be as high as 5 mL/min or more, while achieving capture efficiency close to 100%.

The foregoing illustrative embodiment is described generally in terms of the induction of the expression of a common antigen 211 by one or more different unknown pathogen 211, as shown in FIG. 2. The invention generally provides methods of using a vector or viral preparation 207 to cause unknown pathogens 201 to present a common binding element.

Figure 3:
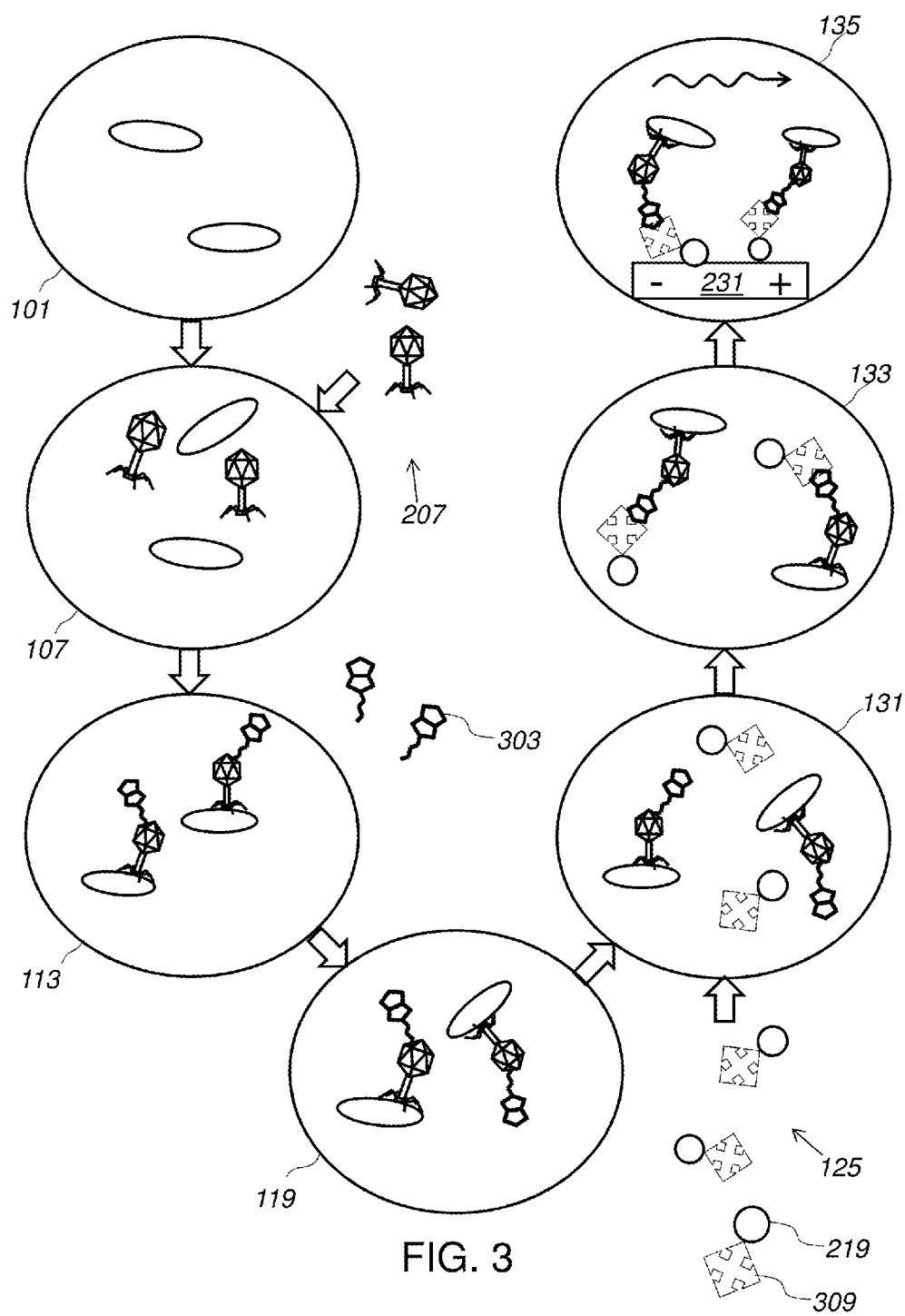
FIG. 3 shows using a viral preparation to biotinylate different unknown pathogens.

FIG. 3, for example, illustrates an alternative embodiment of a method of using a viral preparation 207 to cause different unknown pathogens to present 119 a common binding element 303. As shown in FIG. 3, viral preparation 207 includes at least one phage.

In certain embodiments, a bacteriophage is used that expresses a biotin binding domain (aka, a biotinylation peptide) on at least one capsid protein. The phage contains the genetic information to display a biotinylation domain and be biotinylated. In some embodiments, the phage displays a biotinylation domain when introduced 107 into the sample. When the phage attach to cells 201, those cells are then biotinylated. In certain embodiments, the phage infects the target cells and progeny virions produced from the infection will have been biotinylated by the target cells' 201 biotin ligase protein (BLP). Biotinylation of phage with biotinylation peptides on their capsids is discussed in Edgar et al., 2006, High-sensitivity bacterial detection using biotin-tagged phage and quantum-dot nanocomplexes, PNAS 103 (13):4841-4945 and Gervias et al., 2007, Immobilization of biotinylated bacteriophages on biosensor surfaces, Sensors and Actuators B 125:615-621, each of which are incorporated by reference. Methods of labeling targets, e.g., including biotinylation of phage, are discussed in U.S. Pat. Nos. 7,517,643; 6,342,588; and U.S. Pub. 2011/0086338, the contents and methods of each are incorporated by reference in their entirety for all purposes. In some embodiments, phage capsid is streptavidin or avidin-linked and substrate 219 is biotinylated, as discussed in U.S. Pat. No. 6,740,492, the contents of each are incorporated by reference in their entirety for all purposes.

With continued reference to FIG. 3, cells 201 present 119 biotin 303 as a common binding element. Binding partner 125 is introduced. Here, binding partner 125 includes streptavidin 309 coated beads 219. Biotinylation of phage is further discussed in Smelyanski and Gershoni, 2011, Site directed biotinylation of filamentous phage structural proteins, Virol J 8:495; U.S. Pat. No. 5,994,519; and U.S. Pub. 2001/0019820, the contents and methods of each are incorporated by reference in their entirety for all purposes.

Biotinylated target cells 201 are incubated 131 with streptavidin-coated beads 219. The binding partner binds 133 to the target, after which the target 201 can be isolated 135. For example, where beads 219 are magnetic, a magnet 231 can be used to hold cells 201 in a fluidic channel while the sample is washed away. With reference back to FIG. 1, where live cells are intended 139, the sample can be replaced with a maintenance buffer 147. In an alternative embodiment, cells 201 can be lysed 155, optionally using a lysis buffer 151. In some embodiments, a component of the cells 201 is extracted. For example, DNA may optionally be extracted by column separation 159.

While discussed above in the illustrative embodiments involving biotinylated phage, streptavidin-linked phage, or expression of a common antigen after transduction by a phage, methods of the invention include any suitable method or phenomenon to cause different unknown pathogens 201 to exhibit a common binding element through the introduction of a viral preparation 207. In some embodiments, phage display of an antigen is employed.

Figure 4:
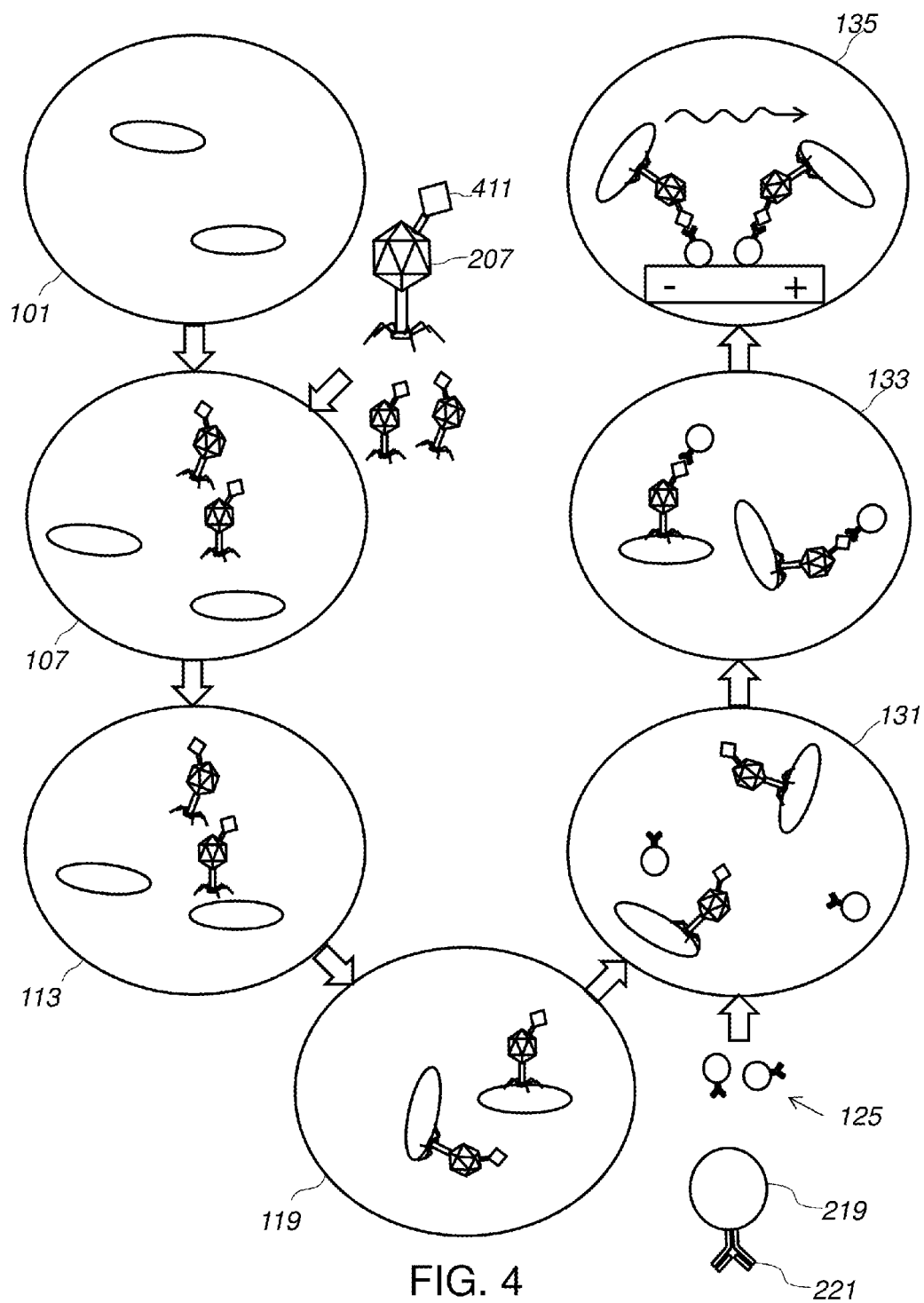
FIG. 4 illustrates phage display of a common antigen by different unknown pathogens.

FIG. 4 illustrates phage display of a common antigen by different unknown pathogens 201. In phage display, a gene for antigen 411 is ligated into the phage genome, for example, within the gene encoding one of the coat proteins, or capsid proteins. Multiple cloning sites may be used to ensure in-frame cloning and proper expression of the protein product. The viral preparation 207 including one or more phage engineered for phage display of a common antigen 411 is then introduced 107 into the sample containing unknown pathogens 201. A binding partner is used (e.g., linked to a substrate 219 such as a well in a microtitre plate, a surface of a fluidic channel, beads in a column, or magnetic beads) that binds to antigen 411. After the phage attach 119 to pathogens 201, they display antigen 411. Phage display is discussed in Haq, 2012, Bacteriophages and their implications on future biotechnology, a review, Virol J 9:9; U.S. Pat. No. 8,227,242 (e.g., phage display without helper phage); U.S. Pat. Nos. 8,216,797; 7,238,669; 6,740,492; U.S. Pub. 2010/0240579 (detection of unknown target by phage display); and U.S. Pub. 2006/0063149, the contents of which are incorporated by reference.

In some embodiments, phage display antigen 411 when introduced 107 into the sample. In certain embodiments, the genetically-engineered phage is introduced and infects pathogens 201 and generates progeny virions that express antigen 411. Viral preparation 207 may include a bacterial growth medium to allow low concentrations (e.g., single cells) of target to grow and be infected and propagate the phage. Moreover, a combination of the foregoing may occur in that phage may exhibit antigen 411 upon introduction 107 into the sample, and may infect and propagate, generating progeny.

While any suitable substrate 219 may be used, and any suitable binder (e.g., aptamers, co-factors, proteins, etc.), in certain embodiments, magnetic beads linked to antibody 221 are used. This binding partner 125 is introduced into the infected sample and allowed to incubate 131.

FIG. 3 shows that incubation 131 leads to the binding 133 of binding partner 125 to antigen 411 on cells 201. After cells 201 are bound to magnetic beads 219 via antibody 221/antigen 411 interaction, the cells 201 may be isolated 135 from the sample by magnetic separation. Further, additional steps may be performed to optimize the isolation or extraction of cells 201 from the sample. Additional steps optionally include washing with one or more solutions, further concentrating 139 captured cells (e.g., using a magnetic concentrator), introduction of additional buffers such as, for example, cell maintenance buffers or lysis buffers, other suitable processes known in the art, or a combination thereof.

Other methods of using a binding partner to capture a target are operable with methods of the invention. For example, where pathogens 201 are intracellular parasites, a known binding element may be associated with the host cells. A binding partner may be used that would not be able to target an unknown pathogen directly but instead bind to the host (if the host is eukaryotic, instead of a phage viral preparation, a binding partner specific to a eukaryotic protein may be employed). See, e.g., Drancourt et al., 1992, Diagnosis of Mediterranean spotted fever by indirect immunofluorescence of *Rickettsia conorii* in circulating endothelial cells isolated with monoclonal antibody-coated immunomagnetic beads, J Inf Dis 166:660-3, incorporated by reference. Optionally, the membrane of the eukaryotic host can be ruptured (e.g., with detergent, a virus or particle, differential osmolality, etc.,) and the infectious agent targeted by methods herein. In some embodiments, methods of the invention may be used in combination with, or in sequence with, alternative methodologies that would only operate, for example, where one or more target is known. If a target is known, it may exhibit a known binding element that can be captured with a binding partner. See, e.g., Fu et al., Rapid detection of *E. coli* O157:H7 by immunomagnetic separation and real-time PCR, incorporated by reference.

The process of magnetic separation 135 described above (e.g., with respect to FIG. 3) produces efficient capture of different unknown pathogens 201 and the removal of all or majority of the remaining components in the mixture. However, it is still possible that a relatively small amount of non-specific analytes are unintentionally captured along with the target/magnetic particle complexes. It may be desired to remove these non-specific analytes. Accordingly, the surface may be washed with a wash solution that reduces particle aggregation, thereby isolating target/magnetic particle complexes from the non-specific target entities.

Any wash solution that does not disrupt interaction between the binding partner of the magnetic particle and the target may be used. The wash solution should also not disrupt the capture of the target/particle complexes on the intended surface. Exemplary solutions include heparin, Tris-HCl, phosphate buffered saline (PBS), Tris-borate-EDTA (TBE), Tris-acetate-EDTA (TAE), Tris-cacodylate, HEPES, or similar. One or more wash cycle may be performed. For embodiments in which the sample includes blood, heparin may be used to inhibit clotting. The bound targets are washed with heparin-containing buffer 1-3 times to remove blood components and to reduce formation of aggregates. Methods for these steps are described in U.S. Pat. No. 7,776,580; U.S. Pub. 2011/0263833; U.S. Pub. 2011/0262989; U.S. Pub. 2011/0262933; U.S. Pub. 2011/0262927; U.S. Pub. 2011/0262893; and U.S. Pub. 2010/0092956, the contents of which are incorporated by reference for all purposes.

Once the different unknown pathogens 201 have been isolated 135, they may be preserved as living cells or they may be lysed and the lysate, or a component thereof, may be detected, extracted, isolated, quantified, or used.

Where live cells are intended 141, a live cell buffer may be introduced 147, for example, in a step that includes flushing away any wash buffers, other solutions or reagents, or remaining components of the sample.

Once the target/magnetic particles have been captured, the target is then lysed 155. In certain embodiments, lysis of the target occurs without separating the particles from the target prior to the lysis step. Conducting the lysis without the pre-separation step allows more efficacious collection of analytes contained within the target. For instance, if the analyte of interest is a bacterially-derived nucleic acid, some analyte may be lost when bacteria separated from the magnetic particles are inadvertently lost. With the disclosed methods, the bacteria are still bound to the particles and captured on a surface as lysis occurs. Accordingly, there is a concentrated sample to work with during the lysis step. In addition, the disclosed methods allow for recovery of a specific analyte in a relatively small collection volume. This is especially useful when the analyte of interest is a nucleic acid or something that is similarly present in only very small quantities. For example, one could begin with a blood sample of 2 ml and use the described methods to concentrate a desired pathogen from the blood onto an appropriate surface. With the pathogen captured, one could decant the blood, add 0.3 ml of a suitable buffer, and subsequently perform the lysis step.

Lysis 155 can be performed using any means known in the art. For example, lysis could be performed using 151 a lysis buffer (see, e.g., FIG. 1). Any type of lysis buffer is suitable for use with the disclosed methods; selection of the specific buffer may depend on the subsequent analysis of the cell lysate. Buffer selection is within the general skill of the art and can be determined empirically. Generally, lysis buffers contain Tris-HCL, EDTA, EGTA, SDS, deoxycholate, Triton X, and/or NP-40. In some cases the buffer may also contain NaCl (e.g., 150 mM). In certain aspects, the lysis buffer is a chaotropic solution.

Lysis 155 can also be achieved through, or assisted by, sonication. In this method, the captured target/magnetic particle complexes are exposed to ultrasonic waves to achieve lysis of any target (bacteria, cells, virus, fungi, etc.) associated with the magnetic particles so that any analytes of interest contained therein are released. In some embodiments, the analyte of interest can include a nucleic acid.

The methods described herein can be used in accordance with any sonication device, which are well-known in the art. In certain embodiments, the sonication device is the VCX 750 Sonicator sold under the trademark VIBRA-CELL (sonicator, commercially available from Sonics and Materials, Inc.). Generally, the probe of the sonicator is placed into the liquid containing the targets to be lysed. Electrical energy from a power source is transmitted to a piezoelectric transducer within the sonicator converter, where it is changed to mechanical vibrations. The longitudinal vibrations from the converter are intensified by the probe, creating pressure waves in the liquid. These in turn produce microscopic bubbles, which expand during the negative pressure excursion and implode violently during the positive excursion. This phenomenon, referred to as cavitation, creates millions of shock waves and releases high levels of energy into the liquid, thereby lysing the target. In another embodiment, the sonication transducer may be brought in contact with a chamber holding captured complexes by way of a structural interface. The sonication transducer vibrates the structural interface such that lysis is achieved. In either method, the appropriate intensity and period of sonication can be determined empirically by those skilled in the art.

The lysate containing the contents of the lysed target can then be eluted. In certain aspects, the lysate contains nucleic acids of interest associated with a particular bacteria present in the starting sample. The lysate is removed from the magnetic particles and the analytes contained therein can be analyzed. Analytes may include, without limitation, nucleic acids, proteins, organelles, and other components found within the target of interest.

The analyte may be analyzed by a multitude of existing technologies, such as NMR, Polymerase Chain Reaction (PCR), sequencing, mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components. Analysis using NMR is described in U.S. Pub. 2011/0262925, herein incorporated by reference in its entirety. In some embodiments, the different unknown pathogens 201 are analyzed in order to identify genes they express. For example, captured bacteria 201 are lysed without first separating the bacteria from the magnetic particles. The lysate is then eluted from the magnetic particles and DNA contained within the lysate/eluate is bound to DNA extraction resin. After washing of the resin, the bacterial DNA is eluted and used in quantitative RT-PCR to detect the presence of a specific species, and/or, subclasses of bacteria.

Detection of bacteria of interest can be performed by use of nucleic acid probes following procedures which are known in the art. Suitable procedures for detection of bacteria using nucleic acid probes are described in U.S. Pat. Nos. 7,943,346; 5,620,847; 5,569,586; 5,541,308; 5,401,631; 5,089,386; and 5,055,394, each of which is hereby incorporated by reference.

A suitable nucleic acid probe assay generally includes sample treatment and lysis, hybridization with selected probe(s), hybrid capture, and detection. Lysis 155 of the bacteria is necessary to release the nucleic acid for the probes. In accordance with the invention, a means for lysing the bacteria is introduced while the bacteria are still bound to the magnetic particle and the resulting complexes have been captured on a surface. There is no separation of the bacteria from the magnetic particles prior to lysis. In some embodiments, the nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. In other embodiments, sonication is used to lyse the cells. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labeled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Bacterially-derived nucleic acids isolated from the lysate can be used as templates for the PCR reaction. PCR can also include the use of reverse-transcriptase PCR (RT-PCR), in which RNA isolated from the target is reverse transcribed into its DNA complement (i.e., cDNA) using the enzyme reverse transcriptase, and the resulting cDNA is amplified using PCR. RT-PCR is described in detail in U.S. Pub. 2011/0071033, incorporated by reference herein in its entirety.

In certain embodiments, differential gene expression associated with the target can also be identified, or confirmed using a microarray technique. In this method, polynucleotide sequences of interest (including cDNAs and oligonucleotides) are plated, or arrayed, on a microchip substrate. The arrayed sequences are then hybridized with specific DNA probes from cells or tissues of interest. Methods for making microarrays and determining gene product expression (e.g., RNA or protein) are shown in U.S. Pub. 2006/0195269, the content of which is incorporated by reference herein in its entirety.

In particular aspects, nucleic acids isolated from the target can be sequences to generate a plurality of sequence reads, thereby identifying a pathogen according to a known genetic sequence. Sequencing may be by any method known in the art. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes. Methods of sequencing are discussed in U.S. Pat. No. 8,209,130 and U.S. Pub. 2011/0071033, the content of which is incorporated by reference herein in its entirety.

In certain embodiments, methods of the invention are useful for direct detection of unknown bacteria 201 from blood. Such a process is described here. Sample is collected in sodium heparin tube by venipuncture, acceptable sample volume is about 1 mL to 10 mL. Sample is diluted with binding buffer and superparamagnetic particles having binding partners are added to the sample, followed by incubation on a shaking incubator at 37° C. for about 30 min to 120 min. Alternative mixing methods can also be used. In a particular embodiment, sample is pumped through a static mixer, such that reaction buffer and magnetic particles are added to the sample as the sample is pumped through the mixer. This process allows for efficient integration of all components into a single fluidic part, avoids moving parts and separate incubation vessels and reduces incubation time.

Capture of the labeled targets allows for the removal of blood components and reduction of sample volume from 30 mL to 5 mL. The capture is performed in a variety of magnet/flow configurations. In certain embodiments, methods include capture in a fluidic cartridge or other flow-through device at flow rate of 5 mL/min, resulting in total capture time of 6 min.

After capture, the captured target is washed with wash buffer including heparin to remove blood components and free particles. The composition of the wash buffer is optimized to reduce aggregation of free particles, while maintaining the integrity of the particle/target complexes.

After the wash step, the still captured targets are sonicated in order to lyse the cells. The bacterial cells are not separated from the magnetic particles prior to sonication. While the appropriate settings for sonication can be determined empirically, a sonicator can be used for a duration of 3 minutes to achieve effective lysis. The resulting lysate can then be eluted and the expression profile of any nucleic acid found in the lysate can be determined.

Devices for conducting the above methods are also provided. Any suitable device or system may be used. In general, the devices comprise an input channel, an output channel, a chamber, a magnetic assembly, and a lysing device. The input channel and output channel are in fluid communication with the chamber and the magnetic assembly is adapted to capture a magnetic particle inputted into the input channel onto a surface of the chamber. The lysing device is adapted to lyse a target bound to the magnetic particle. In one illustrative embodiment, the device is a fluidic cartridge.

Figure 5:
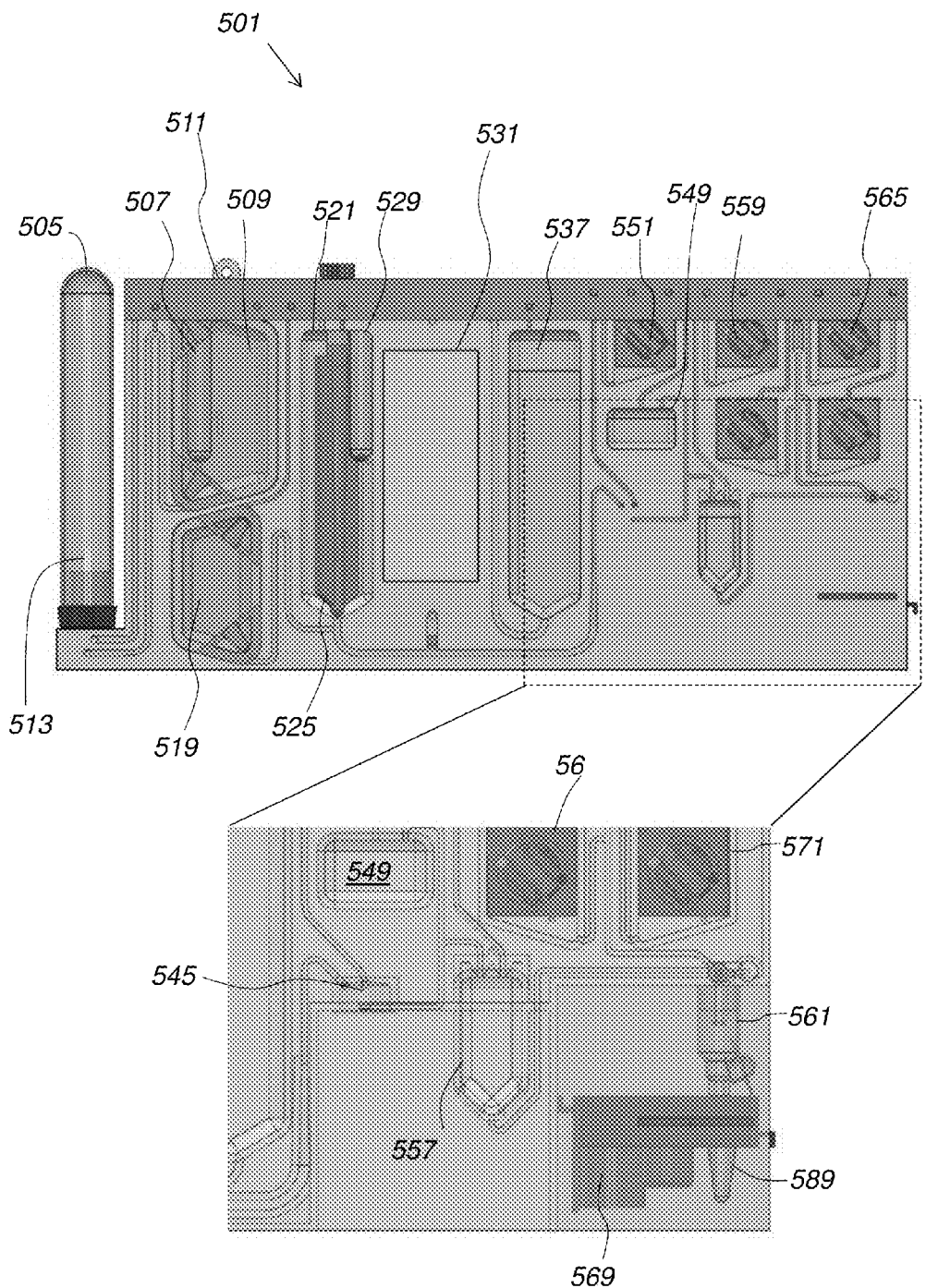
FIG. 5 illustrates a fluidic cartridge according to certain embodiments.

FIG. 5 illustrates a fluidic cartridge 501 according to certain embodiments. Fluidic cartridge 501 is provided to operate with blood collection tube 505 (e.g., a vacutainer). Cartridge 501 includes long needle 513 that penetrates into an interior of tube 505 when tube 505 is inserted thereon. Magnetic beads are stored in magnetic bead ampule 507 shown disposed within bead buffer 509. Pneumatic interface 511 provides pressure to flow sample, solutions, and buffers through channels of cartridge 501 and may optionally be used to crush ampules such as magnetic bead ampule 507 (and plant pathogen ampule 529). When operation is begun and tube 505 containing a sample is inserted, magnetic bead ampule 507 is crushed, introducing beads 219 to bead buffer 509. Beads 219 and buffer 509 may be mixed, for example, using agitation provided by air from pneumatic interface 511, to produce a bead mixture.

Air from pneumatic interface 511 forces blood from tube 505 into mixing chamber 521. The bead mixture is forced through long needle 513 to rinse the inside of tube 505. The bead mixture is then sent to mixing chamber 521 to mix with the blood. This step may be repeated, sending more bead mixture from bead buffer 509, through tube 505, to mixing chamber 521, until tube 505 is evacuated of target and a desired proportion (e.g., 2:1) of bead mixture to sample is present in mixing chamber 521.

Mixing paddle 525 is used to mixing the contents of chamber 521, agitating the blood and beads. Air pressure from pneumatic interface 511 then forces the mixture into magnetic trap 531. Optionally, the mixture can be pushed back, from magnetic trap 531 to mixing chamber 521, and the cycle repeated any number times until mixing chamber 521 is satisfactorily evacuated of target pathogens 201 and the bead-bound target pathogens 201 as well as the other components of the sample are in magnetic trap 431.

Then, magnetic trap 431 is evacuated of the other components of the sample, leaving magnetic particles 219 bound to magnets therein. The waste fluid is pushed back through mixing chamber 521 and discarded. Wash buffer 519 is then forced into magnetic trap 531, filling it. The wash buffer can then be pushed back to mixing chamber 521 to ensure good washing of beads 219. Wash buffer is sent back into magnetic trap 531 and held there.

Magnets can then be moved away from magnetic trap 531, allowing beads 219 to re-suspend in wash buffer 519 within trap 531. At this point, target pathogens 201 have been extracted from the original sample and held in wash buffer 519. Wash buffer 519 can then be pushed through magnetic concentrator 545 to waste chamber 549.

Turning now to the inset portion of FIG. 5, magnetic concentrator 545 can be seen to be in fluid communication with magnetic trap 531. As wash buffer 519 flows through concentrator 545, beads 219 are captured in concentrator 545 while the remainder of buffer 519 is passed on to waste chamber 549. Original pathogens 201 are thus concentrated in concentrator 545.

The contents of concentrator 545 may be processed according to whether live cells or an extracted cellular component is intended. If live cells are intended, the magnet is removed from magnetic concentrator 545 and buffer 551 (here, a live cell buffer) is introduced through concentrator 545 and used to flush the cells into output vial 589.

If, for example, extracted DNA is intended, buffer 551 is a lysis buffer and is introduced into magnetic concentrator 545. The magnet is removed from concentrator 545 and a sonicator may be applied to a wall of the chamber of concentrator 545. Optionally, beads may be included for bead-bashing to aid in lysis. The sonicator or other lysis means is activated and the target cells 201 are lysed. In certain embodiments, a probe of a sonicator extends into the chamber, where it delivers vibrations into the liquid medium surrounding the captured complexes. In other embodiments, the sonication transducer is brought in contact with the chamber by way of a structural interface. For example, the structural interface may constitute the floor or the ceiling of the chamber. The sonication transducer vibrates the structural interface such that lysis of the targets captured in the chamber is achieved.

Lysate is then pushed into pre-column mixer 557. DNA binding buffer 559 is added to pre-column mixer 557 (optionally agitated by bubbling air). The contents of pre-column mixer 557 is then forced through the DNA extraction column 561 and the elutant is discarded as waste. DNA extraction may be completed using washes from first column wash 565, second column wash 569, and water 571. Air from pneumatic interface 511 can be forced through DNA extraction column 561 to remove volatile organic compounds. Water 571 can be used to rinse the purified DNA (optionally including the use of a de-binding buffer or a modulator of stringency) into output vial 589.

Coordination of the on-cartridge steps can be supported by an operations device, such as a bench-top electro-mechanical device. The timing of pneumatic injections, the breaking of ampules, and the piercing of reagent reservoirs can be coordinated manually, or by a computer program or mechanical system. Cartridge 501 can include any suitable materials, shape, or dimensions. For example, in some embodiments, fluids are handled in macrofluidic environments up until entered into magnetic concentrator 545 and are handled according to microfluidic principles thereafter. In general, microfluidic may refer to sub-microliters volumes.

Figure 6:
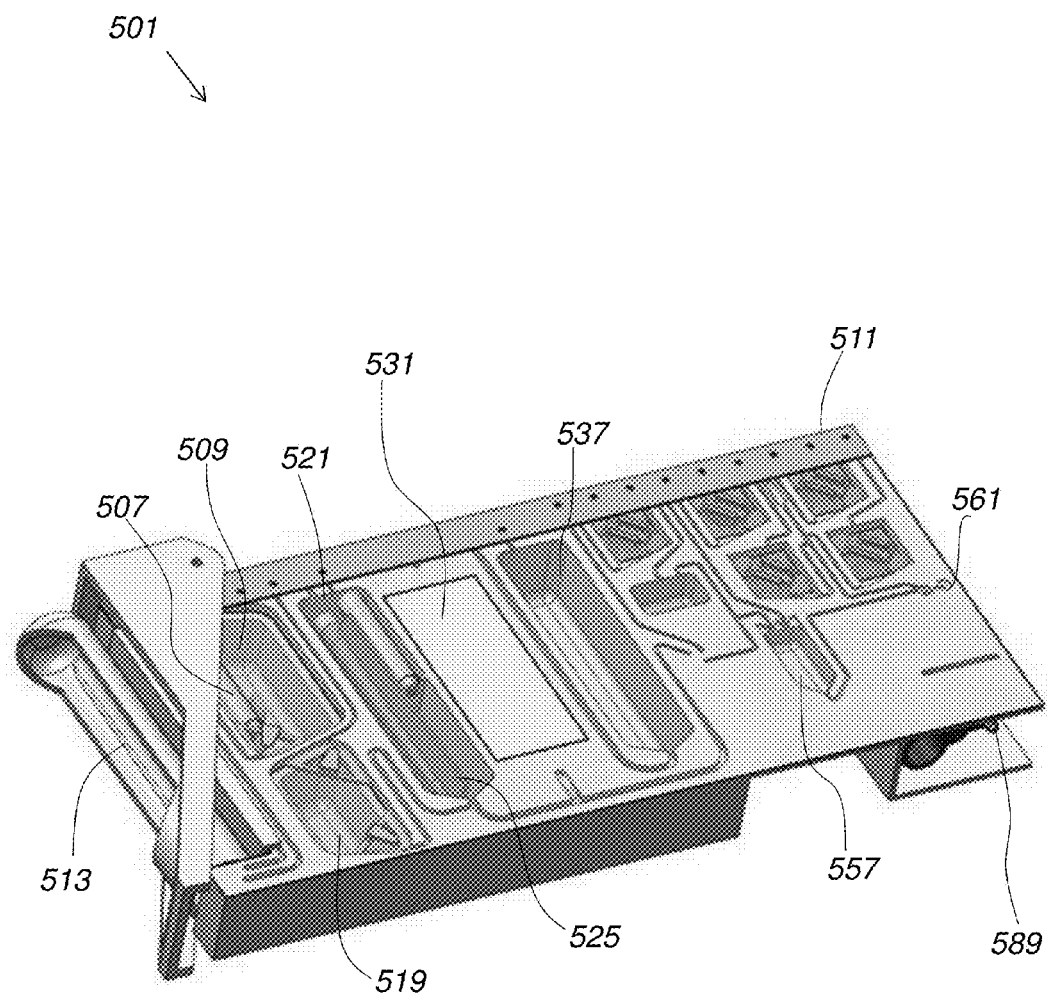
FIG. 6 gives a perspective view of the cartridge shown in FIG. 5.

FIG. 6 gives a perspective view of an exemplary cartridge according to certain embodiments. Methods for manufacturing and operating fluidic systems are known and discussed in Fredrickson and Zan, 2004, Macro-to-micro interfaces for microfluidic devices, Lab Chip 4(6):526-33; U.S. Pat. Nos. 8,105,783; 7,785,869; 7,745,207; 7,553,647; U.S. Pub. 2009/0227005; U.S. Pub. 2008/0241000; and U.S. Pub. 2008/0003564, the contents of each of which are incorporated by reference in their entirety for all purposes.

Figure 7:
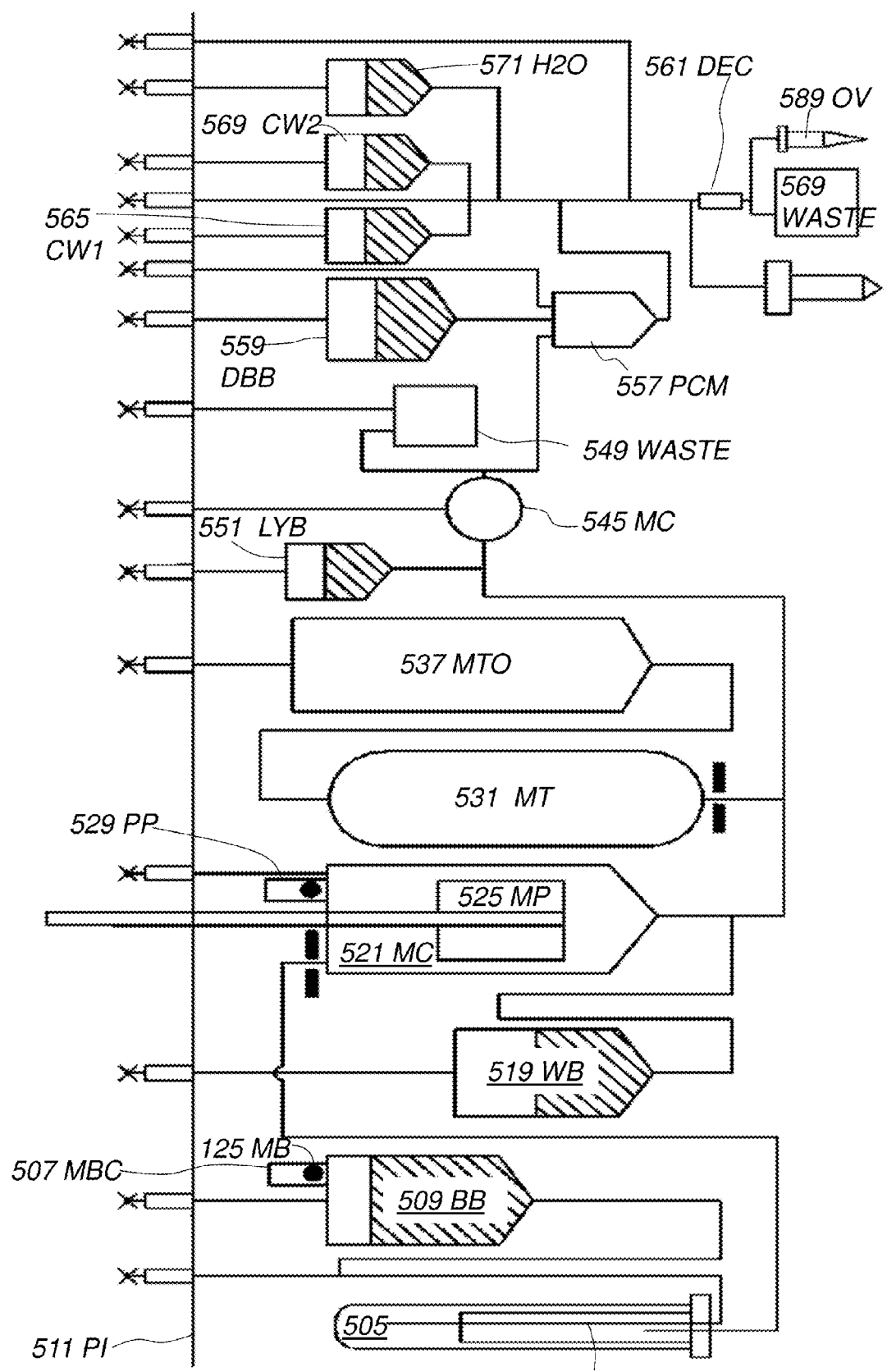
FIG. 7 gives a schematic diagram of the cartridge shown of FIG. 5.

FIG. 7 gives a schematic diagram of elements and steps of the invention as discussed above with respect to FIG. 5.

While discussed above as magnetic beads, substrate 219 for capture of pathogens 201 may be the floor of a chamber such as, for example, trap chamber 531. In other embodiments, the capture surface is the ceiling. The captured pathogens 201 can there be washed to remove non-specific analytes and unbound entities.

In certain embodiments, fluidic cartridge 501 is designed to be disposable. In this instance, once pathogens 201 have been lysed and the eluate collected, cartridge 501 can be discarded. In this manner, each cartridge is intended for a single use, and the potential for cross-contaminating pathogens due to repeated use is eliminated.

The cartridge can be prepared from any material in the art suitable for containing liquids and withstanding the rigors of sonication. In certain aspects, the entire cartridge is made of plastic or an acrylic plastic polymer. In other aspects, the bottom or top cover of the cartridge can be prepared from a film such as the biaxially-oriented polyethylene terephthalate (BoPET) sold under the trademark MYLAR while the rest of the cartridge is made of plastic or an acrylic plastic polymer. In certain embodiments, the BoPET film constitutes the aforementioned structural interface in contact with the sonicator transducer.

In certain embodiments, the cartridge is connected to a fluidic device or system configured to flow liquids into and out of the cartridge. The fluidic system can comprise a pump that delivers liquid, air, gas, beads, reagents, electricity or other signals, light, power or a combination thereof to the cartridge. The fluidic system can have a first tubing line connected to the inlet of the input channel, for flowing liquid into the cartridge. The other end of the first tubing line is connected to the pump. A second tubing line for fluid leaving the cartridge is connected to the outlet of the output channel. The other end of the second tubing line may also be connected to the pump or to a container for collecting exiting fluid. The fluidic system facilitates the delivery of the target/magnetic particle complexes into the chamber, as well as any washing of captured complexes. The collection of lysate is also facilitated by the fluidic system.

Devices of the invention may also include a detection module. The detection module is a component in which molecules, cells, or other particles are to be detected, identified, measured or interrogated on the basis of at least one predetermined characteristic. The molecules, cells, or other particles can be examined one at a time, and the characteristic is detected or measured optically, for example, by testing for the presence or amount of a label. In some aspects, the detection module is in connection with one or more detection apparatuses. The detection apparatuses can be optical or electrical detectors or combinations thereof. Examples of suitable detection apparatuses include optical waveguides, microscopes, diodes, light stimulating devices (e.g., lasers), photomultiplier tubes, and processors (e.g., computers and software), and combinations thereof, which cooperate to detect a signal representative of a characteristic, marker, probe, label, or reporter, and to determine and direct a measurement or sorting action. However, other detection techniques can be used as well.

Devices of the invention may include a computer component. For example, a user interface may be provided with input/output mechanisms (monitor, keyboard, touchscreen, etc.) coupled to a memory and a processor (e.g., a silicone chip and a solid-state or magnetic hard drive). Input/output mechanisms may be included for data, such as a USB port, Ethernet port, or Wi-Fi card or a hardware connection to a detection module, fluidic chip and pneumatic interface, or both.

In certain aspects, the detection module is in fluid connection with the fluidic cartridge. For example, the outlet of the fluidic cartridge may be connected to the detection module by means of a tubing line. In this manner, lysate leaving the cartridge can enter the detection module wherein the contents of the lysate can be detected and analyzed.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

I claim:

1. A method of isolating a microorganism in a sample, the method comprising:
   obtaining a sample suspected of containing two or more microorganisms;
   introducing to the sample two or more viruses, each virus capable of causing a different microorganism to present a surface element;
   exposing the sample to one or more capture moieties that bind the surface elements presented on the microorganisms, thereby forming capture moiety/microorganism complexes; and
   isolating the capture moiety/microorganism complexes from the sample.

2. The method of claim 1, wherein the two or more viruses cause the two or more microorganisms to display the same element.

3. The method of claim 1, wherein the two or more viruses cause the two or more microorganisms to each display a different element.

4. The method of claim 1, wherein at least one of said two or more viruses is a bacteriophage.

5. The method of claim 2, wherein the element is a cell surface protein.

6. The method of claim 3, wherein the different elements comprise different cell surface proteins.

7. The method of claim 1, wherein the one or more capture moieties comprise one or more antibodies.

8. The method of claim 4, wherein said bacteriophage contains a biotinylation domain.

9. The method of claim 1, wherein the at least one of the one or more capture moieties comprises streptavidin.

10. The method of claim 1, wherein at least one of the two or more microorganisms is a bacteria.

11. The method of claim 1, wherein at least one of the two or more microorganisms is a fungus.

12. The method of claim 1, wherein the two or more microorganisms are present in the sample at as low as 1 CFU/mL.

13. The method of claim 1, wherein the one or more capture moieties are bound to magnetic particles.

14. The method of claim 13, wherein said isolating step comprises applying a magnetic field.

* * * * *